(12) United States Patent
Zakharenko et al.

(10) Patent No.: US 10,696,972 B2
(45) Date of Patent: Jun. 30, 2020

(54) METHOD FOR IMPROVING LEARNING

(71) Applicant: St. Jude Children's Research Hospital, Inc., Memphis, TN (US)

(72) Inventors: Stanislav S. Zakharenko, Collierville, TN (US); Jay A. Blundon, Memphis, TN (US)

(73) Assignee: ST. JUDE CHILDREN'S RESEARCH HOSPITAL, INC., Memphis, TN (US)

( * ) Notice: Subject to any disclaimer, the term of this patent is extended or adjusted under 35 U.S.C. 154(b) by 320 days.

(21) Appl. No.: 15/551,659

(22) PCT Filed: Feb. 18, 2016

(86) PCT No.: PCT/US2016/018377
§ 371 (c)(1),
(2) Date: Aug. 17, 2017

(87) PCT Pub. No.: WO2016/134091
PCT Pub. Date: Aug. 25, 2016

(65) Prior Publication Data
US 2018/0030453 A1 Feb. 1, 2018

Related U.S. Application Data

(60) Provisional application No. 62/118,245, filed on Feb. 19, 2015, provisional application No. 62/142,521, filed on Apr. 3, 2015.

(51) Int. Cl.
| | | |
|---|---|---|
| *A01N 43/04* | (2006.01) | |
| *A61K 31/70* | (2006.01) | |
| *C12N 15/113* | (2010.01) | |
| *A61K 31/713* | (2006.01) | |
| *A61K 31/7072* | (2006.01) | |
| *A61K 31/7105* | (2006.01) | |
| *A61K 31/416* | (2006.01) | |
| *A61K 31/4545* | (2006.01) | |
| *G09B 5/00* | (2006.01) | |
| *G09B 19/00* | (2006.01) | |

(52) U.S. Cl.
CPC ........ *C12N 15/1138* (2013.01); *A61K 31/416* (2013.01); *A61K 31/4545* (2013.01); *A61K 31/7072* (2013.01); *A61K 31/713* (2013.01); *A61K 31/7105* (2013.01); *G09B 5/00* (2013.01); *G09B 19/00* (2013.01); *C12N 2310/14* (2013.01)

(58) Field of Classification Search
None
See application file for complete search history.

(56) References Cited

U.S. PATENT DOCUMENTS

| | | |
|---|---|---|
| 5,954,630 A | 9/1999 | Masaki et al. |
| 8,382,484 B2 | 2/2013 | Wetmore et al. |
| 2002/0165197 A1 | 11/2002 | Fishman et al. |
| 2004/0248909 A1* | 12/2004 | Sun ........................ A61K 31/00 514/263.33 |

OTHER PUBLICATIONS

Haghdoost-Yazdi et al. Behavioural Brain Research (2012), vol. 233(2), pp. 375-381.*
Littwitz et al. Pflugers Arch.—Eur. J. Physiol. (2011), vol. 461, pp. 165.*
Yoon, Jenny Nam. "Music in the Classroom: Its Influence on Children's Brain Development, Academic Performance, and Practical Life Skills." (2000).*
Marek Neuropharmacology (2009), vol. 56, pp. 1082-1087.*
Kalk et al. British Journal of Pharmacology (2007), vol. 151, pp. 1025-1032.*
Akahane et al. J. Med. Chem. (1999), vol. 42, pp. 779-783.*
Lu et al. Purinergic Signalling (2014), vol. 10, pp. 619-629.*
Zlomuzica et al. Purigenic Signalling (2013), vol. 9, pp. 175-182.*
Bakin, J. S. et al, "Induction of a physiological memory in the cerebral cortex by stimulation of the nucleus basalis," Proc. Natl. Acad. Sci. USA (1996), vol. 93, pp. 11219-11224.
Bao, S. et al., "Cortical remodelling induced by activity of ventral tegmental dopamine neurons," Nature (2001), vol. 412, pp. 79-83.
Barkat, T. R. et al., "A critical period for auditory thalamocortical connectivity," Nature Neuroscience (2011), vol. 14, No. 9, pp. 1189-1194.
Blundon, J. A. et al., "Presynaptic Gating of Postsynaptic Synaptic Plasticity: A Plasticity Filter in the Adult Auditory Cortex," The Neuroscientist (2013), vol. 19, No. 5, pp. 465-478.
Blundon, J. A., et al., "Presynaptic Gating of Postsynaptically Expressed Plasticity at Mature Thalamocortical Synapses," The Journal of Neuroscience (2011), vol. 31, No. 44, pp. 16012-16025.
Chun, S. et al., "Thalamocortical Long-Term Potentiation Becomes Gated after the Early Critical Period in the Auditory Cortex," The Journal of Neuroscience (2013), vol. 33, No. 17, pp. 7345-7357.
Crair, M. C. et al., "A critical period for long-term potentiation at thalamocortical synapses," Nature (1995), vol. 375, pp. 325-328.
De Villers-Sidani, E. et al., "Critical Period Window for Spectral Tuning Defined in the Primary Auditory Cortex (A1) in the Rat," The Journal of Neuroscience (2007), vol. 27, No. 1, pp. 180-189.
Dunwiddie, T. V. et al., "The role and regulation of adenosine in the central nervous system," Annu. Rev. Neurosci. (2001), vol. 24, pp. 31-55.
Feldman, D. E. et al., "Map plasticity in somatosensory cortex," Science (2005), vol. 310, pp. 810-815.

(Continued)

*Primary Examiner* — Patrick T Lewis
(74) *Attorney, Agent, or Firm* — Troutman Sanders LLP

(57) ABSTRACT

The invention is directed to a method for improving learning and/or memory (e.g., auditory, visual, somatosensory or motor) in adults and children of an age which is beyond the early critical period for learning, said method comprising inhibiting (i) ecto-5'-nucleotidase (Nt5e, aka CD73) or (ii) A1 adenosine receptor (A1R, aka Adora1) expression or function in the brain. The invention is also directed to a method for treating learning and memory defects and neurological diseases associated with an abnormal auditory, visual, or somatosensory perception by inhibiting Nt5e or A1R expression or function in the brain.

24 Claims, 6 Drawing Sheets

Specification includes a Sequence Listing.

(56) References Cited

OTHER PUBLICATIONS

Froemke, R. C. et al., "A synaptic memory trace for cortical receptive field plasticity," Nature (2007), vol. 450, pp. 425-429.

Froemke, R. C., et al. "Long-term modification of cortical synapses improves sensory perception," Nature Neuroscience (2013), vol. 16, No. 1, pp. 79-88.

Guo, Z. V., et al. "Flow of cortical activity underlying a tactile decision in mice," Neuron (2014), vol. 81, pp. 179-194.

Hackett, T. A., et al., "Linking topography to tonotopy in the mouse auditory thalamocortical circuit," The Journal of Neuroscience(2011), vol. 31, No. 8, pp. 2983-2995.

Han, Y. K. et al., "Early experience impairs perceptual discrimination," Nature Neuroscience (2007), vol. 10, No. 9, pp. 1191-1197.

Hubener, M. et al., "Neuronal Plasticity: Beyond the Critical Period," Cell (2014), vol. 159, pp. 727-737.

Insanally, M. N. et al., "Feature-dependent sensitive periods in the development of complex sound representation," The Journal of Neuroscience (2009), vol. 29, No. 17, pp. 5456-5462.

Johansson, B., et al. "Hyperalgesia, anxiety, and decreased hypoxic neuroprotection in mice lacking the adenosine A1 receptor," Proc. Natl. Acad. Sci. USA (2001), vol. 98, No. 16, pp. 9407-9412.

Kilgard, M. P. et al., "Cortical map reorganization enabled by nucleus basalis activity," Science (1998), vol. 279, pp. 1714-1718.

Manzoni, O. J. et al., "Release of adenosine by activation of NMDA receptors in the hippocampus," Science (1994), vol. 265, pp. 2098-2101.

Mitchell, J. B. et al., "Activity-dependent release of endogenous adenosine modulates synaptic responses in the rat hippocampus," The Journal of Neuroscience (1993), vol. 13, No. 8, pp. 3439-3447.

Oberlaender, M. et al., "Sensory experience restructures thalamocortical axons during adulthood," Neuron (2012), vol. 74, pp. 648-655.

O'Connor, D. H., et al. "Vibrissa-based object localization in head-fixed mice," The Journal of Neuroscience (1947), vol. 30, No. 5, pp. 1947-1967.

Pani, A. K. et al., "Neurochemical measurement of adenosine in discrete brain regions of five strains of inbred mice," PLoS One (2014), vol. 9, Issue 3, p. e92422.

Polley, D. B. et al., "Multiparametric auditory receptive field organization across five cortical fields in the albino rat," J. Neurophysiol (2007), vol. 97, pp. 3621-3638.

Prusky, G. T. et al., "Behavioral assessment of visual acuity in mice and rats," Vision Research (2000), vol. 40, pp. 2201-2209.

Recanzone, G. H. et al., "Plasticity in the frequency representation of primary auditory cortex following discrimination training in adult owl monkeys," The Journal of Neuroscience (1993), vol. 13, No. 1, pp. 87-103.

Reed, A. et al., "Cortical map plasticity improves learning but is not necessary for improved performance," Neuron (2011), vol. 70, pp. 121-131.

Rowland, N. E. et al., "Feeding behavior, obesity, and neuroeconomics," Physiology & Behavior (2008), vol. 93, pp. 97-109.

Schreiner, C. E. et al., "Auditory map plasticity: diversity in causes and consequences," Current Opinion in Neurobiology (2014), vol. 24, pp. 143-156.

Street, S. E. et al., "Tissue-nonspecific alkaline phosphatase acts redundantly with PAP and NT5E to generate adenosine in the dorsal spinal cord," The Journal of Neuroscience (2013), vol. 33, pp. 11314-11322.

Takesian, A. E. et al., "Balancing plasticity/stability across brain development," Progress in Brain Research (2013), vol. 207, 32 pages.

Thompson, L. F. et al., "Crucial role for ecto-5'-nucleotidase (CD73) in vascular leakage during hypoxia," The Journal of Experimental Medicine (2004), vol. 200, No. 11, pp. 1395-1405.

Trevino, M. "Stimulus similarity determines the prevalence of behavioral laterality in a visual discrimination task for mice," Scientific Reports (2014), vol. 4, 7569, 12 pages.

Trevino, M. et al., "Alpha-1 adrenergic receptors gate rapid orientation-specific reduction in visual discrimination," Cerebral Cortex (2012), vol. 22, pp. 2529-2541.

Ward, R. D. et al., "Modeling motivational deficits in mouse models of schizophrenia: behavior analysis as a guide for neuroscience," Behavioural Processes (2011), vol. 87, pp. 149-156.

Yawo, H. et al., "Preferential inhibition of omega-conotoxin-sensitive presynaptic Ca2+ channels by adenosine autoreceptors," Nature (1993), vol. 365, pp. 256-258.

Zhang, L. I. et al, "Persistent and specific influences of early acoustic environments on primary auditory cortex," Nature Neuroscience (2001), vol. 4, No. 11, pp. 1123-1130.

Chassan, R., "Adenosine Production Is Essential for Closing the Critical Period of Cortical Plasticity", A Dissertation Presented for The Graduate Studies Council, The University of Tennessee Health Science Center (published Jun. 2, 2014), 36 pages.

Lu, M. et al., "PQ-69, a novel and selective adenosine A1 receptor antagonist with inverse agonist activity", Purinergic Signalling (2014), vol. 10, pp. 619-629.

International Search Report and Written Opinion Issued in International Patent Application No. PCT/US2016/018377, dated May 20, 2016, 10 pages.

King, Andrew J., "Visual influences on auditory spatial learning", Philosophical Transactions of the Royal Society B. (2009), vol. 364, pp. 331-339.

Kandel, S. et al., "Prefrontal Cortex, Hippocampus, and the Biology of Explicit Memory Storage" The McGraw Hill Companies, 5th edition, Principles of Neural Science, Chapter 67 (2012) 35 pages total.

\* cited by examiner

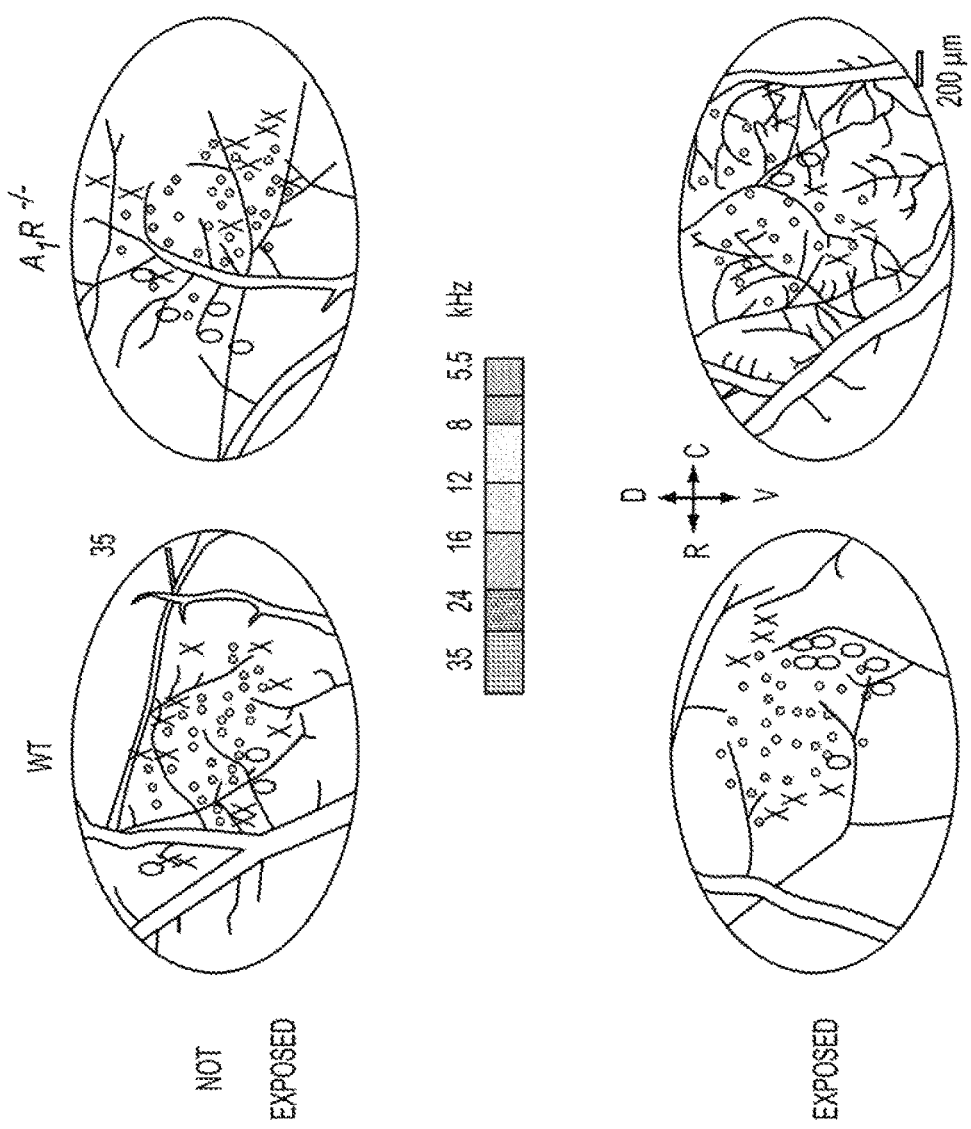
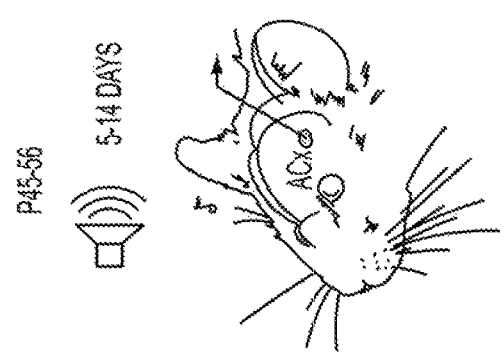
FIG. 1A
FIG. 1B

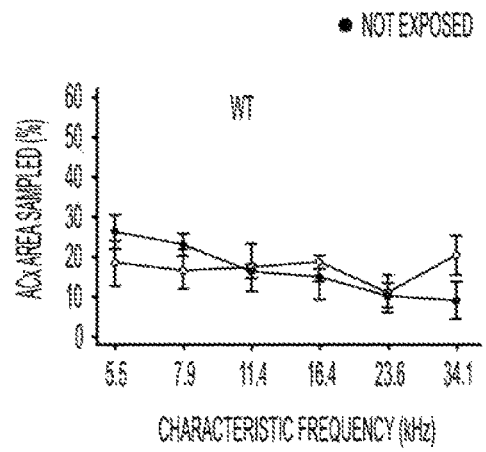
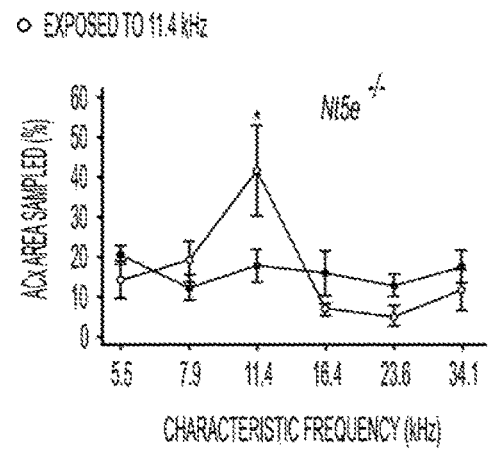
FIG. 2E
FIG. 2F
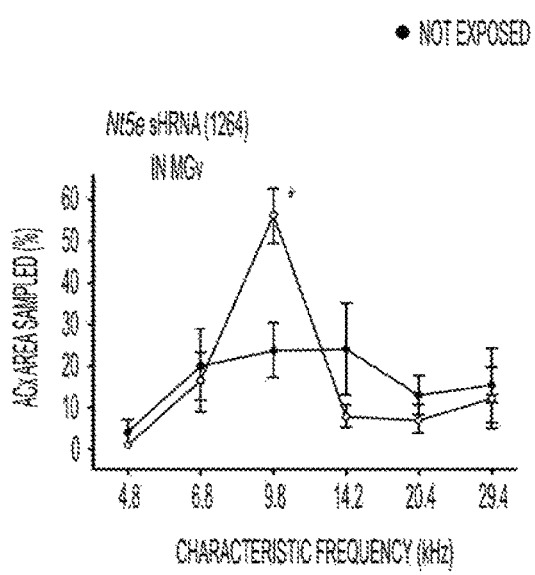
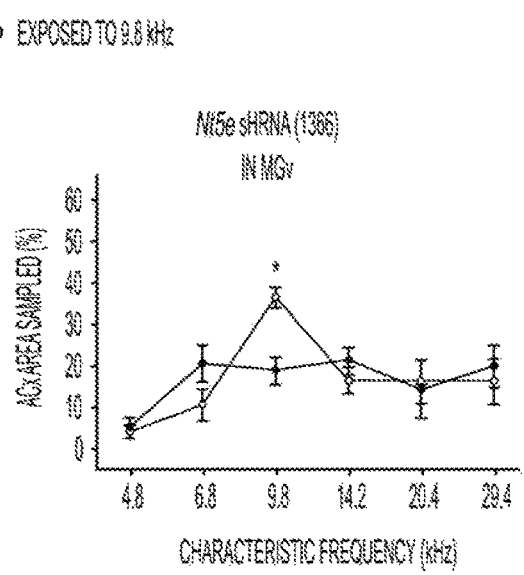
FIG. 2G
FIG. 2H

METHOD FOR IMPROVING LEARNING

CROSS-REFERENCE TO RELATED APPLICATIONS

This application is the U.S. National Phase of International Patent Application No. PCT/US2016/018377, filed on Feb. 18, 2016, which published as International Publication No. WO 2016/134091 A1 on Aug. 25, 2016, and claims priority to US Provisional Application Ser. No. 62/142,521, filed on Apr. 3, 2015 and U.S. Provisional Application Ser. No. 62/118,245, filed on Feb. 19, 2015, all of which are incorporated herein by reference in their entirety.

STATEMENT AS TO FEDERALLY SPONSORED RESEARCH

This invention was made with government support under grant DC012833 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 2, 2016, is named 243734-000074 SL.txt and is 3,270 bytes in size.

FIELD OF THE INVENTION

The invention is directed to a method for improving learning and/or memory (e.g., auditory, visual, somatosensory, or motor) in adults and children of an age which is beyond the early critical period for said learning, said method comprising inhibiting (i) ecto-5'-nucleotidase (Nt5e, aka CD73) and/or (ii) A1 adenosine receptor (A1R, aka Adora1) expression or function in the brain. The invention is also directed to a method for treating learning and memory defects and neurological diseases associated with an abnormal auditory, visual, or somatosensory perception by inhibiting Nt5e and/or A1R expression or function in the brain.

BACKGROUND OF THE INVENTION

Virtually all animals can alter their behavior based on past experience. What underlies this ability to acquire, store, and retrieve information is synaptic plasticity, whereby existing connections among neurons are strengthened or weakened and new synapses are formed or existing ones removed. The capacity for synaptic plasticity and, by consequence, for learning and memory is not constant throughout life; it often peaks relatively soon after birth and then typically declines, at variable rates, with increasing age. In many brain systems and animals, there are distinct phases of greatly enhanced plasticity for specific sensory experiences or sensory-motor interactions. Neuronal plasticity is particularly prominent in the developing brain. On the other hand, synaptic plasticity in the adult brain is widespread and is a key feature of many brain regions, like the hippocampus, the striatum, or the cerebellum. Thus, although neuronal plasticity is certainly much more profound in the developing brain than in adulthood, it is not exclusively restricted to that period.

Acoustic experiences change cortical maps in the auditory cortex (ACx), and these changes are required for auditory cognition[1-3]. During an early critical period (a few neonatal days in rodents), passive exposure to a tone of certain frequencies expands the ACx areas that are tuned to those frequencies[4-7]. This cortical map plasticity is restricted in adults[3,8,9]. Restrictive mechanisms that control the duration of the early critical period and impede cortical map plasticity in adults are still being debated[2,10-14].

In rodents, the early critical period for ACx map plasticity and thalamocortical (TC) connectivity is restricted to a few early postnatal (P) days[4]. Long-term synaptic plasticity, in the form of long-term potentiation (LTP) or long-term depression (LTD), at TC projections has been implicated as a cellular mechanism of cortical map plasticity in the ACx. TC LTP and LTD are also restricted to the early critical period[15-17]. Like ACx map plasticity[8,18,19], LTP and LTD can be unmasked at TC projections in adults if the activation of TC projections is paired with that of cholinergic projections emanating from the nucleus basalis[10,15,16].

Adenosine, which is released in an activity-dependent manner[20-22] and is a negative regulator of neurotransmitter release at excitatory synapses through activation of $A_1$ adenosine receptor $(A_1R)$[23], appears to be an important intermediate of cholinergic modulation of TC synaptic plasticity[10].

The adenosine A1 receptor (A1R) is one member of the adenosine receptor group of G protein-coupled receptors with adenosine as endogenous ligand. A1R is widely distributed throughout the central nervous system (CNS), with the highest levels occurring in the cerebral cortex, hippocampus, cerebellum, thalamus, brain stem, and spinal cord of the rat. A1R is coupled to pertussis toxin-sensitive Gi-proteins to inhibit adenylate cyclase. The most prominent effect of A1R on the brain is to depress excitatory transmission. At the presynaptic site, A1R activation inhibits synaptic transmission by the suppression of N-type calcium channels and by a direct downregulation of the release apparatus. At postsynaptic sites, A1Rs are located in the postsynaptic density where they can influence the responsiveness to excitatory stimuli by a simultaneous control of N-type calcium channels and N-methyl-D-aspartate receptors (NMDARs). In addition, A1R in neuronal cells is also located nonsynaptically where activation of A1Rs results in G-protein-dependent activation of inwardly rectifying K+ channels (GIRKs), leading to hyperpolarization of the resting membrane potential. Thus, the A1R can affect neuronal excitability and control of "basal" synaptic transmission (i.e., under conditions where synaptic plasticity is not engaged) by the activation of A1R located presynaptically and postsynaptically as well as nonsynaptically. Reviewed, e.g., in Chen, Int. Rev. Neurobiol., 2014, 119:257-307, Ch. 12.

Ecto-5'-nucleotidase (Nt5e; EC 3.1.3.5) catalyzes the conversion of purine 5'-mononucleotides to nucleosides, the preferred substrate being AMP. The enzyme consists of a dimer of 2 identical 70-kD subunits bound by a glycosyl phosphatidyl inositol linkage to the external face of the plasma membrane.

SUMMARY OF THE INVENTION

There is a great need in the art to find ways to improve learning and memory beyond the early critical period in children (i.e., beyond 5 years of age in humans) and especially in adults. The present invention addresses this and other needs by providing a method for improving learning and/or memory (e.g., auditory, visual, somatosensory [tactile] or motor) in a subject in need thereof comprising administering to said subject an inhibitor of expression or function of (i) ecto-5'-nucleotidase (Nt5e, aka CD73) or (ii)

A1 adenosine receptor (A1R, aka Adora1), wherein said inhibitor is administered in an amount which is effective for inhibiting expression or function of Nt5e or A1R in the brain. In one specific embodiment, the invention provides a method for improving learning and/or memory of an acoustic information (e.g., language or music) in a subject in need thereof comprising administering to said subject an inhibitor of expression or function of Nt5e or A1R), wherein said inhibitor is administered in an amount which is effective for inhibiting expression or function of Nt5e or A1R in the brain. In one specific embodiment, the subject is simultaneously exposed to (i) an inhibitor of Nt5e or A1R and (ii) to a sound (this can be achieved, e.g., by first administering the inhibitor to the subject and then exposing the subject to the sound at around the time when the inhibitor reaches the effective concentration in the brain).

There is a great need in the art to treat learning disorders (e.g., childhood learning disorders, wherein the subject has an impaired ability to learn) and neurological diseases associated with abnormal auditory, visual, or somatosensory (tactile) perception (such as, e.g., Williams-Beuren syndrome, tinnitus, schizophrenia, amblyopia, bipolar disorder, schizoaffective disorder, 22q11 deletion syndrome, and autism spectrum disorders). The present invention addresses this and other needs by providing a method for treating a learning disorder or a neurological disease associated with an abnormal auditory, visual, or somatosensory perception in a subject in need thereof comprising administering to said subject an inhibitor of expression or function of Nt5e or A1R, wherein said inhibitor is administered in an amount which is effective for inhibiting expression or function of Nt5e or A1R in the brain.

In one aspect, the invention provides a method for improving learning and/or memory in a subject in need thereof comprising administering to said subject an inhibitor of expression or function of (i) ecto-5′-nucleotidase (Nt5e) or (ii) A1 adenosine receptor (A1R), wherein said inhibitor is administered in an amount which is effective for inhibiting expression or function of Nt5e or A1R in the brain. In one embodiment, the learning and memory are selected from the group consisting of auditory, visual, somatosensory, and motor.

In one embodiment, the invention provides a method for improving learning and/or memory of an acoustic information in a subject in need thereof comprising administering to said subject an inhibitor of expression or function of (i) ecto-5′-nucleotidase (Nt5e) or (ii) A1 adenosine receptor (A1R), wherein said inhibitor is administered in an amount which is effective for inhibiting expression or function of Nt5e or A1R in the brain. In one specific embodiment, the acoustic information is language or music. In one specific embodiment, the subject is simultaneously exposed to (i) the Nt5e or A1R inhibitor and (ii) to a sound (e.g., the sound in the range 20 Hz-20 kHz). In one specific embodiment, the method comprises first administering the inhibitor to the subject and then exposing the subject to the sound at around the time when the inhibitor reaches the effective concentration in the brain.

In one embodiment of the any of the above methods, the subject is an adult or a child of an age which is beyond the early critical period for said learning.

In one embodiment of the any of the above methods, the subject is human. In one specific embodiment, the subject is a child older than 5 years.

In one embodiment of the any of the above methods, the subject is an experimental animal model.

In another aspect, the invention provides a method for treating a learning disorder or a neurological disease associated with an abnormal auditory, visual, or somatosensory perception in a subject in need thereof comprising administering to said subject an inhibitor of expression or function of (i) ecto-5′-nucleotidase (Nt5e) or (ii) A1 adenosine receptor (A1R), wherein said inhibitor is administered in an amount which is effective for inhibiting expression or function of Nt5e or A1R in the brain. In one embodiment, the neurological disease is selected from the group consisting of tinnitus, Williams-Beuren syndrome, schizophrenia, amblyopia, bipolar disorder, schizoaffective disorder, 22q11 deletion syndrome, and autism spectrum disorders.

In one embodiment, the invention provides a method for treating a learning disorder or a neurological disease associated with an abnormal auditory perception in a subject in need thereof comprising administering to said subject an inhibitor of expression or function of (i) ecto-5′-nucleotidase (Nt5e) or (ii) A1 adenosine receptor (A1R), wherein said inhibitor is administered in an amount which is effective for inhibiting expression or function of Nt5e or A1R in the brain. In one specific embodiment, the neurological disease is selected from the group consisting of tinnitus, Williams-Beuren syndrome, and schizophrenia.

In one embodiment of the above treatment methods, the subject is human. In one embodiment of the above treatment methods, the subject is an experimental animal model.

In one embodiment of any of the above methods, the inhibitor is selected from the group consisting of interfering RNA molecules, dsRNA, RNA polymerase III transcribed DNAs, ribozymes, and antisense nucleic acids. In one specific embodiment, the inhibitor is siRNA or shRNA.

In one embodiment of any of the above methods, the inhibitor is a compound having a structure according to Formula

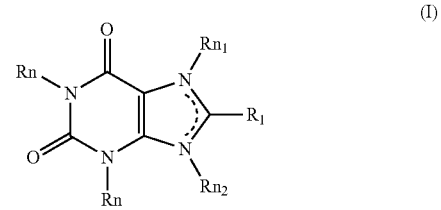

(I)

wherein $R_1$ is selected from hydrogen, —F; —Cl; —Br; —I; —OH, —OR*; —NH$_2$; —NHR*; —N(R*)$_2$; —N(R*)$_3^+$; —SH; —SR*; —CN; —NC; —(C=O)—R*; —CHO; —CO$_2$H; —CO$_2$; —CO$_2$R*; —(C=O)—S—R*; —O—(C=O)—H; —O—(C=O)—R*; —S—(C=O)— R*; —(C=O)—NH$_2$; —(C=O)—N(R*)$_2$; —SCN; —NCS; —NSO; —SO$_2$—R*; —O—S(=O)$_2$—R*; —S(=O)$_2$—OR*; —N$_2$—R*; —N(C$_2$H$_4$); —Si(R*)$_3$; —CF$_3$; —O—CF$_3$; —PR*$_2$; —O—P(=O)(OR*)$_2$; —P(=O)(OR*)$_2$; perfluoroalkyl; an aliphatic $C_1$-$C_{20}$ hydrocarbon radical; a $C_1$-$C_{12}$ aromatic hydrocarbon radical; or a $C_1$-$C_{12}$ heteroaryl radical; where R* is independently at each occurrence hydrogen or a straight chained, branched, or cyclic $C_1$-$C_{20}$ hydrocarbon radical, which is saturated, partially saturated, or aromatic, each of which is optionally substituted with 1-6 heteroatoms selected from nitrogen, oxygen, sulfur, phosphorus, or halogen;

$R_n$ is independently at each occurrence selected from hydrogen or a straight chained, branched, or cyclic saturated, partially saturated, or aromatic $C_1$-$C_{20}$ hydrocarbon radical, optionally substituted with 1-12 heteroatoms selected from nitrogen, oxygen, sulfur, phosphorus, or halogen;

$Rn_1$ is selected from Rn or, if $Rn_2$ is present, $Rn_1$ is a bond, i.e. $Rn_1$ is altogether absent; and $Rn_2$ is selected from Rn or, if $Rn_1$ is present, $Rn_2$ is a bond, i.e. $Rn_2$ is altogether absent; and pharmaceutically acceptable salts thereof. In one specific embodiment, the inhibitor is a compound having a structure according to Formula Ia:

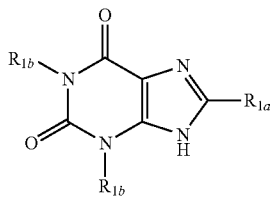
(Ia)

wherein $R_{1a}$ is selected from hydrogen, an aliphatic $C_1$-$C_{20}$ hydrocarbon radical; a $C_1$-$C_{12}$ aromatic hydrocarbon radical; or a $C_1$-$C_{12}$ heteroaryl radical, or a combination thereof; and $R_{1b'}$ is independently at each occurrence selected from hydrogen; —F; —Cl; —Br; —I; —OH, —OR*; —NH$_2$; —NHR*; —N(R*)$_2$; a straight chained, branched, or cyclic saturated, partially saturated, or aromatic $C_1$-$C_{16}$ hydrocarbon radical, or where R* is independently at each occurrence hydrogen or a straight chained, branched, or cyclic $C_1$-$C_{20}$ hydrocarbon radical, which is saturated, partially saturated, or aromatic, each of which is optionally substituted with 1-6 heteroatoms selected from nitrogen, oxygen, sulfur, phosphorus, or halogen, and pharmaceutically acceptable salts thereof. In another specific embodiment, the inhibitor is a compound having a structure according to Formula Ib:

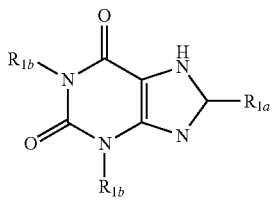
(Ib)

wherein $R_{1a}$ is selected from hydrogen, an aliphatic $C_1$-$C_{20}$ hydrocarbon radical; a $C_1$-$C_{12}$ aromatic hydrocarbon radical, or a $C_1$-$C_{12}$ heteroaryl radical, or a combination thereof; and $R_{1b'}$ is independently at each occurrence selected from hydrogen; —F; —Cl; —Br; —I; —OH, —OR*; —NH$_2$; —NHR*; —N(R*)$_2$; a straight chained, branched, or cyclic saturated, partially saturated, or aromatic $C_1$-$C_6$ hydrocarbon radical, or where R* is independently at each occurrence hydrogen or a straight chained, branched, or cyclic $C_1$-$C_{20}$ hydrocarbon radical, which is saturated, partially saturated, or aromatic, each of which is optionally substituted with 1-6 heteroatoms selected from nitrogen, oxygen, sulfur, phosphorus, or halogen, and pharmaceutically acceptable salts thereof. In yet another specific embodiment, the inhibitor is a compound having a structure selected from Formulas Ic-Ir:

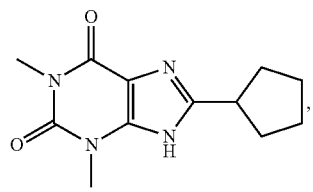
(Ic)

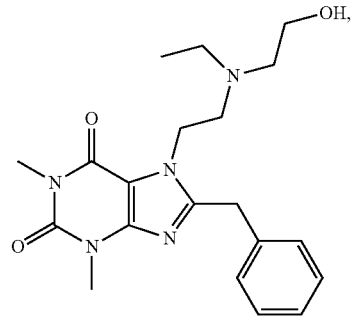
(Id)

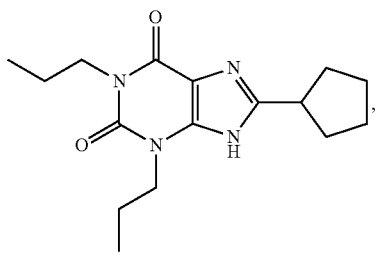
(Ie)

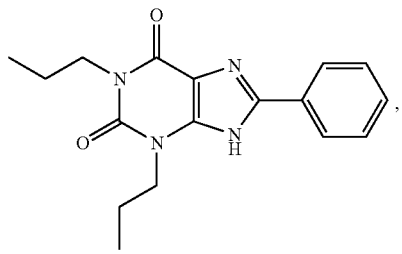
(If)

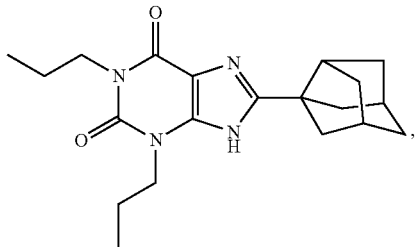
(Ig)

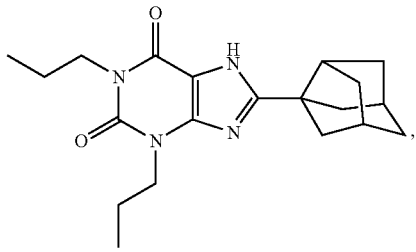
(Ih)

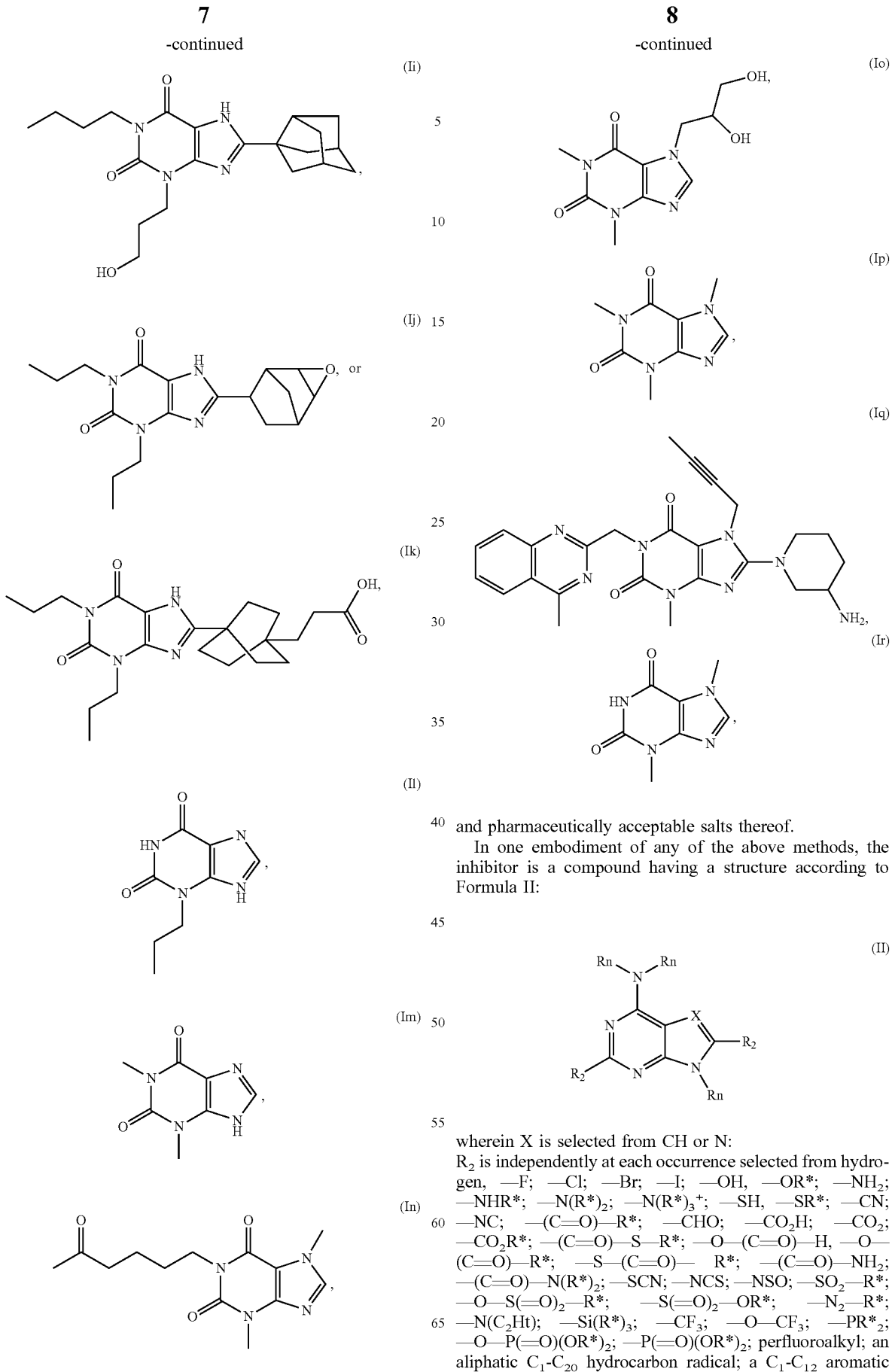

and pharmaceutically acceptable salts thereof.

In one embodiment of any of the above methods, the inhibitor is a compound having a structure according to Formula II:

(II)

wherein X is selected from CH or N:
$R_2$ is independently at each occurrence selected from hydrogen, —F; —Cl; —Br; —I; —OH, —OR*; —NH$_2$; —NHR*; —N(R*)$_2$; —N(R*)$_3^+$; —SH, —SR*; —CN; —NC; —(C=O)—R*; —CHO; —CO$_2$H; —CO$_2^-$; —CO$_2$R*; —(C=O)—S—R*; —O—(C=O)—H, —O—(C=O)—R*; —S—(C=O)— R*; —(C=O)—NH$_2$; —(C=O)—N(R*)$_2$; —SCN; —NCS; —NSO; —SO$_2$—R*; —O—S(=O)$_2$—R*; —S(=O)$_2$—OR*; —N$_2$—R*; —N(C$_2$Ht); —Si(R*)$_3$; —CF$_3$; —O—CF$_3$; —PR*$_2$; —O—P(=O)(OR*)$_2$; —P(=O)(OR*)$_2$; perfluoroalkyl; an aliphatic C$_1$-C$_{20}$ hydrocarbon radical; a C$_1$-C$_{12}$ aromatic hydrocarbon radical; or a $C_1$-$C_{12}$ heteroaryl radical, where R* is independently at each occurrence hydrogen or a straight chained, branched, or cyclic $C_1$-$C_{20}$ hydrocarbon radical, which is saturated, partially saturated, or aromatic, each of which is optionally substituted with 1-6 heteroatoms selected from nitrogen, oxygen, sulfur, phosphorus, or halogen;

Rn is selected from hydrogen or a straight chained, branched, or cyclic saturated, partially saturated, or aromatic $C_1$-$C_{20}$ hydrocarbon radical, or a $C_1$-$C_{20}$ carbohydrate, optionally substituted with 1-12 heteroatoms selected from nitrogen, oxygen, sulfur, phosphorus, or halogen, and pharmaceutically acceptable salts thereof. In one specific embodiment, the inhibitor is a compound having a structure selected from Formulas IIa or IIb:

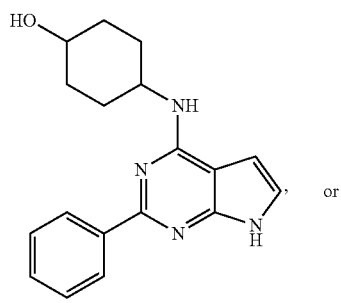

(IIa)

or

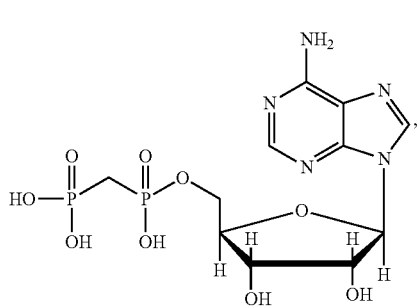

(IIb)

and pharmaceutically acceptable salts thereof. In another specific embodiment, the inhibitor is a compound having a structure selected from Formulas IIc-IIe:

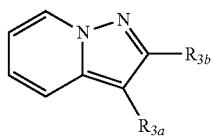

(IIc)

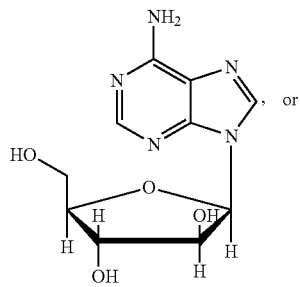

(IId)

or

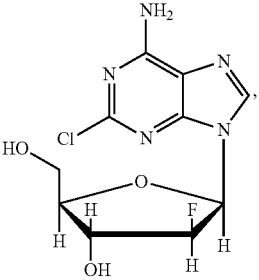

(IIe)

and pharmaceutically acceptable salts thereof.

In one embodiment of any of the above methods, the inhibitor is a compound having a structure according to Formula III:

(III)

wherein $R_{3a}$ and $R_{3b}$ are independently selected from hydrogen, —F; —Cl; —Br; —I; —OH, —OR*; —NH$_2$; —NHR*; —N(R*)$_2$; —N(R*)$_3^+$; —SH; —SR*; —CN; —NC; —(C=O)—R*; —CHO; —CO$_2$H; —CO$_2$; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —SCN; —NCS; —NSO; —SO$_2$—R*; —O—S(=O)$_2$—R*; —S(=O)$_2$—OR*; —N$_2$—R*; —N(C$_2$H$_4$); —Si(R*)$_3$; —CF$_3$; —O—CF$_3$; —PR*$_2$; —O—P(=O)(OR*)$_2$; —P(=O)(OR*)$_2$; perfluoroalkyl; an aliphatic $C_1$-$C_{20}$ hydrocarbon radical; a $C_1$-$C_{12}$ aromatic hydrocarbon radical; or a $C_1$-$C_{12}$ heteroaryl radical, or combinations thereof; where R* is independently at each occurrence hydrogen or a straight chained, branched, or cyclic $C_1$-$C_{20}$ hydrocarbon radical, which is saturated, partially saturated, or aromatic, each of which is optionally substituted with 1-6 heteroatoms selected from nitrogen, oxygen, sulfur, phosphorus, or halogen;

and pharmaceutically acceptable salts thereof. In one specific embodiment, the inhibitor is a compound having a structure according to Formula IIIa:

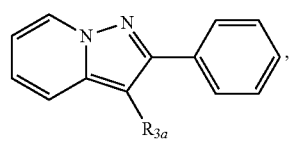
(IIIa)

wherein $R_{3a}$ is selected from hydrogen, acyl, or a $C_1$-$C_{20}$ hydrocarbon radical, which is saturated, partially saturated, or aromatic, each of which is optionally substituted with 1-6 heteroatoms selected from nitrogen, oxygen, sulfur, phosphorus, or halogen. In another specific embodiment, the inhibitor is a compound having a structure selected from Formulas IIIb-IIIh:

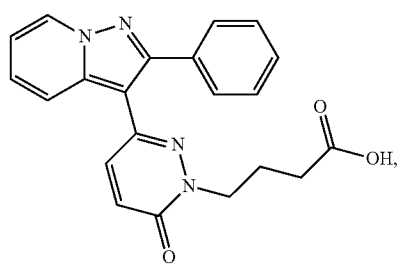
(IIIb)

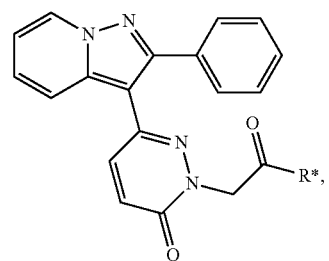
(IIIc)

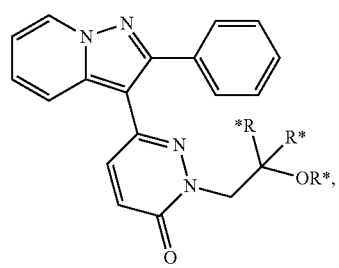
(IIId)

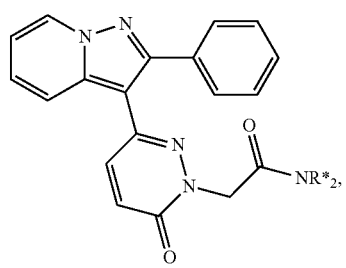
(IIIe)

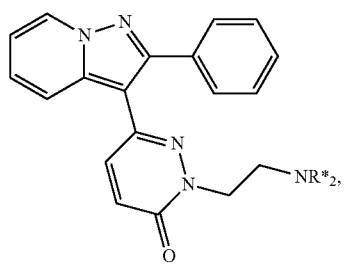
(IIIf)

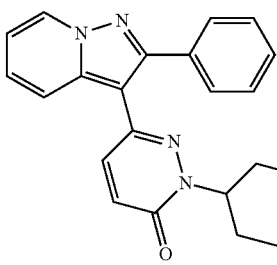
(IIIg)

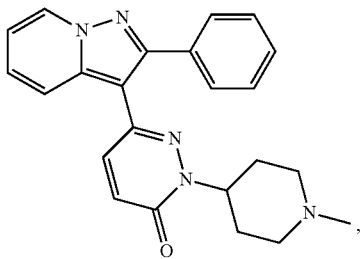
(IIIh)

wherein R* is independently at each occurrence hydrogen or a straight chained, branched, or cyclic $C_1$-$C_{20}$ hydrocarbon radical, which is saturated, partially saturated, or aromatic, each of which is optionally substituted with 1-6 heteroatoms selected from nitrogen, oxygen, sulfur, phosphorus, or halogen. In some embodiments, two R* groups located on the same atom may fuse together to form a $C_1$-$C_8$ ring;

and pharmaceutically acceptable salts thereof. In yet another specific embodiment, the inhibitor is a compound having a structure according to Formula IIIi:

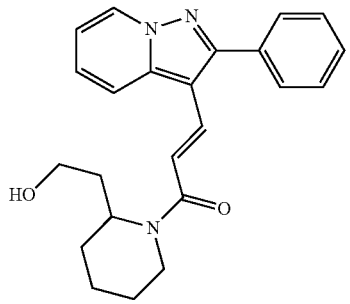
(IIIi)

and pharmaceutically acceptable salts thereof.

In one embodiment of any of the above methods, the inhibitor is a compound having a structure according to Formula IV:

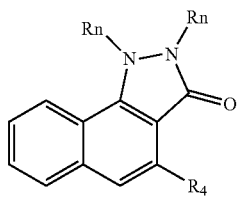

(IV)

wherein $R_4$ is selected from hydrogen, —F; —Cl; —Br; —I; —OH, —OR*; —NH$_2$; —NHR*; —N(R*)$_2$; —N(R*)$_3^+$; —SH; —SR*; —CN. —NC; —(C=O)—R*; —CHO; —CO$_2$H; —CO$_2$; —CO$_2$R*; —(C=O)—S—R*; —O—(C=O)—H; —O—(C=O)—R*; —S—(C=O)— R*; —(C=O)—NH$_2$; —(C=O)—N(R*)$_2$; —SCN; —NCS; —NSO; —SO$_2$—R*; —O—S(=O)$_2$—R*; —S(=O)$_2$—OR*; —N$_2$—R*; —N(C$_2$H$_4$); —Si(R*)$_3$; —CF$_3$; —O—CF$_3$; —PR*$_2$; —O—P(=O)(OR*)$_2$; —P(=O)(OR*)$_2$; perfluoroalkyl; an aliphatic $C_1$-$C_{20}$ hydrocarbon radical; a $C_1$-$C_{12}$ aromatic hydrocarbon radical; or a $C_1$-$C_{12}$ heteroaryl radical; where R* is independently at each occurrence hydrogen or a straight chained, branched, or cyclic $C_1$-$C_{20}$ hydrocarbon radical, which is saturated, partially saturated, or aromatic, each of which is optionally substituted with 1-6 heteroatoms selected from nitrogen, oxygen, sulfur, phosphorus, or halogen;

$R_n$ is independently at each occurrence selected from hydrogen or a straight chained, branched, or cyclic saturated, partially saturated, or aromatic $C_1$-$C_{20}$ hydrocarbon radical, optionally substituted with 1-12 heteroatoms selected from nitrogen, oxygen, sulfur, phosphorus, or halogen;

and pharmaceutically acceptable salts thereof. In one specific embodiment, the inhibitor is a compound having a structure according to Formula IVa:

(IVa)

wherein R* is independently at each occurrence hydrogen, halogen, or a straight chained, branched, or cyclic $C_1$-$C_{20}$ hydrocarbon radical, which may be saturated, partially saturated, or aromatic, each of which may be optionally substituted with 1-6 heteroatoms selected from nitrogen, oxygen, sulfur, phosphorus, or halogen;

and pharmaceutically acceptable salts thereof. In another specific embodiment, the inhibitor is a compound having a structure according to Formula IVb:

(IVb)

and pharmaceutically acceptable salts thereof.

In one embodiment of any of the above methods, the inhibitor is a compound selected from the group consisting of Azelastine, Tetrahydrobiopterin, Silodosin, Pefloxacin, Folic acid, Pomalidomide, Mefloquine, Letrozole, Pemetrexed, Droperidol, and Ticagrelor, and pharmaceutically acceptable derivatives and salts thereof.

These and other aspects of the present invention will be apparent to those of ordinary skill in the art in the following description, claims and drawings.

BRIEF DESCRIPTION OF THE DRAWINGS

FIGS. 1A-1J demonstrate that deletion of $A_1R$ in the auditory thalamus is sufficient for passive exposure to a sound to induce cortical map plasticity in the ACx. FIG. 1A shows a schematic where mature (P45-P56) mice were exposed to a pure tone for 5 to 14 days, and tone-evoked electrophysiological mapping of the ACx was performed. FIG. 1B shows representative ACx maps in WT or $A_1R^{-/-}$ mice that were unexposed (naïve) or exposed to 16.4-kHz tone. Depicted are blood vessels: D, dorsal; V ventral; R, rostral; C, caudal. FIG. 1C shows the percentage of recording sites as a function of characteristic frequencies in the ACx of naïve or pure tone-exposed WT (top) and $A_1R^{-/-}$ (bottom) mice. FIG. 1D shows auditory thalamus (MGv) injections of shRNAs and recordings in the ACx. FIG. 1E shows the percentage of recording sites vs CF in the ACx of naïve and 9.8-kHz tone-exposed WT mice injected with control. FIG. 1F shows the percentage of recording sites vs CF in the ACx of naïve and 9.8-kHz tone-exposed WT mice injected with $A_1R$ shRNA (123). FIG. 1G shows the percentage of recording sites vs CF in the ACx of naïve and 9.8 k-Hz tone-exposed WT mice injected with $A_1R$ shRNA (789). FIG. 1H shows the percentage of recording sites as a function of CF in old (P230-P300) WT mice injected with $A_1R$ shRNA (123) into the MGv. FIG. 1I shows the ACx injections of an $A_1R$ shRNA followed by recordings in the ACx of mature mice. FIG. 1J shows the percentage of recording sites as a function of CF in mature WT mice injected with $A_1R$ shRNA (123) into the ACx. * $p<0.05$.

FIGS. 2A-2H demonstrate that age-dependent elevation of adenosine production underlies cortical map plasticity restrictions in adults. (A) Mean Nt5e, Acpp, and Tnap mRNA levels (normalized to Gapdh) in the auditory thalamus of neonatal or mature mice. (B) Mean Nt5e protein level in the auditory thalamus, ACx, and hippocampus of neonatal or mature mice. (2C, 2D) Total adenosine level in the auditory thalamus, ACx, and hippocampus of neonatal or mature WT (2C) and Nt5e$^{-/-}$ (2D) mice. (2E, 2F) Percentage of recording sites as a function of CF in the ACx of naïve or 11.4 kHz-exposed WT (2E) and Nt5e$^{-/-}$ (2F) mice. (2G, 2H) Percentage of recording sites as a function of CF in the ACx of naïve or 9.8 kHz-exposed WT mice injected into the MGv with Nt5e shRNA (1264) (2G) and Nt5e shRNA (1366) (2H) mice. * p<0.05.

DETAILED DESCRIPTION OF THE INVENTION

Figure 1C:
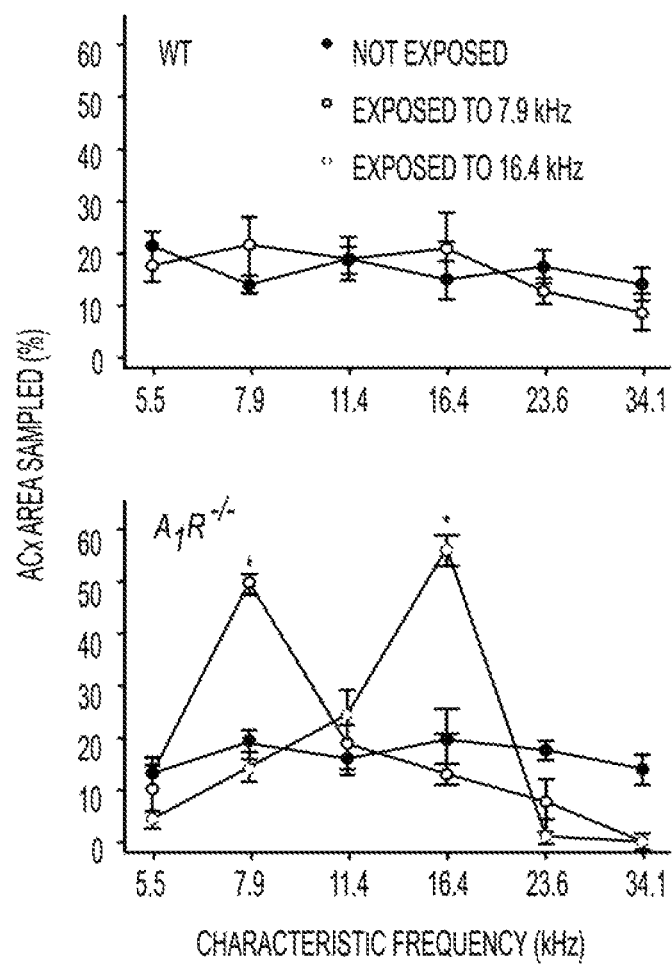

The present invention is based on an unexpected discovery by the inventors that auditory cortical plasticity can be extended long into adulthood by restricting the age-dependent elevation in adenosine production that is mediated by ecto-5'-nucleotidase (Nt5e, also called CD73) and blocking signaling through A1 adenosine receptor (A1R, also called Adora1) in the auditory thalamus. As demonstrated in the Examples section below, deleting or knocking down Nt5e or A1R in thalamocortical (TC) auditory projections in mice was sufficient to shift the auditory cortex (ACx) representation toward the exposed frequency in adults. This shift in tuning occurred at the level of cortical maps and individual neurons, as observed via calcium imaging in vivo, and produced a behavioral response to the exposed sound, which is normally ineffective. Therefore, preventing adenosine production or signaling in the auditory thalamus removes restrictive mechanisms that impede cortical plasticity and rejuvenates auditory learning capabilities in adults.

Definitions

Within the meaning of the present invention, the terms "A1 adenosine receptor", "A1R" and "Adora1" are used interchangeably to refer to one or more protein isoforms (e.g., human variant 1 [GenBank Accession No. NM_000674.2] human variant 2 [GenBank Accession No. NM_001048230.1]; human variant X3 [predicted transcript GenBank Accession No. XM_005244901.1]; human variant X1 [predicted transcript GenBank Accession No. XM_005244899.1]; human variant X4 [predicted transcript GenBank Accession No. XM_005244902.2]).

The terms "ecto-5'-nucleotidase", "Nt5e" and "CD73" are used interchangeably to refer to one or more protein isoforms (e.g., human variant 1 [GenBank Accession No. NM_002526.3]; human variant [[GenBank Accession No. NM_001204813.1]).

The term "inhibitor" as used herein in connection with Nt5e or A1R encompasses direct inhibitors of a function of Nt5e (one or more isoforms) or A1R (one or more isoforms) and inhibitors of expression of Nt5e (one or more isoforms) or A1R (one or more isoforms).

Within the meaning of the present invention, the term "inhibit" is used to refer to any level of reduction in a function or amount of a molecule. The term "inhibit expression" is used to refer to both inhibiting gene expression and inhibiting protein production.

As used herein, the terms "learning disorder" or "learning defect" refer to conditions wherein the subject has an impaired ability to learn. Such learning disorders can be diagnosed, e.g., by using the DSM-V criteria (American Psychiatric Association, 2013, Diagnostic and Statistical Manual of Mental Disorders (Fifth Edition)), which include, e.g., clinical review of the individual's developmental, medical, educational, and family history, reports of test scores and teacher observations, and responses to academic interventions.

The term "sound" is used herein to refer to vibrations of air or other media with frequencies covering the entire hearing range for a given mammal (e.g., 20 Hz-20 kHz for humans, 1 kHz-80 kHz for mice).

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

In the context of the present invention insofar as it relates to any of the disease conditions recited herein, the terms "treat", "treatment", and the like mean to relieve or alleviate at least one symptom associated with such condition, or to slow or reverse the progression of such condition, or to arrest, delay the onset (i.e., the period prior to clinical manifestation of a disease) and/or reduce the risk of developing or worsening a disease. Within the meaning of the present invention, the term "treat" also denotes reducing an abnormal auditory, visual, or somatosensory perception in a subject suffering from a neurological disease.

As used herein the term "therapeutically effective" applied to dose or amount refers to that quantity of a compound or pharmaceutical composition that is sufficient to result in a desired activity upon administration to a subject in need thereof. Note that when a combination of active ingredients is administered (e.g., a combination of two or more inhibitors of Nt5e and/or A1R) the effective amount of the combination may or may not include amounts of each ingredient that would have been effective if administered individually.

The phrase "pharmaceutically acceptable", as used in connection with compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

As used herein, the term "subject" refers to any mammal. In a preferred embodiment, the subject is human.

As used in this specification and the appended claims, the singular forms "a," "an," and "the" include plural references unless the context clearly dictates otherwise.

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements. CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A practical Approach*, Volumes I and II (D. N. Glover ed. 1985); *Oligonucleotide Synthesis* (MJ. Gait ed. 1984); *Nucleic Acid Hybridization* (B. D. Hames & S. J. Higgins eds. (1985>>; Transcription and Translation (B. D. Hames & S. J. Higgins, eds. (1984>>; *Animal Cell Culture* (R. I. Freshney, ed. (1986>>; *Immobilized Cells and Enzymes* (IRL Press, (1986>>; B. Perbal, *A practical Guide To Molecular Cloning* (1984); F. M. Ausubel et al. (eds.), *Current Protocols in Molecular Biology*, John Wiley & Sons, Inc. (1994); among others.

METHODS OF THE INVENTION

In one embodiment, the invention provides a method for improving learning and/or memory (e.g., auditory, visual, somatosensory or motor) in a subject in need thereof (e.g., beyond the early critical period in children and especially in adults) comprising administering to said subject an inhibitor of expression or function of Nt5e or A1R, wherein said inhibitor is administered in an amount which is effective for inhibiting expression or function of Nt5e or A1R in the brain.

In one specific embodiment, the invention provides a method for improving learning and memory of an acoustic information (e.g., language or music) in a subject in need thereof comprising administering to said subject an inhibitor of expression or function of Nt5e or A1R, wherein said inhibitor is administered in an amount which is effective for inhibiting expression or function of Nt5e or A1R in the brain. In one specific embodiment, the subject is simultaneously exposed to (i) an inhibitor of Nt5e or A1R and (ii) to a sound (e.g., 20 Hz-20 kHz for humans; 1 kHz-80 kHz in mice). This can be achieved, e.g., by first administering the inhibitor to the subject and then exposing the subject to the sound at around the time when the inhibitor reaches the effective concentration in the brain.

In another embodiment, the invention provides a method for treating a learning disorder or a neurological disease associated with an abnormal auditory, visual, or somatosensory perception in a subject in need thereof comprising administering to said subject an inhibitor of expression or function of Nt5e or A1R, wherein said inhibitor is administered in an amount which is effective for inhibiting expression or function of Nt5e or A1R in the brain.

In one embodiment of any of the above methods, the subject is human. In another embodiment of any of the above methods, the subject is an experimental animal model.

Non-limiting examples of diseases treatable by the method of the invention include, e.g., tinnitus, Williams-Beuren syndrome, schizophrenia, amblyopia, bipolar disorder, schizoaffective disorder, 22q11 deletion syndrome, and autism spectrum disorders.

It is contemplated that more than one inhibitor of Nt5e and/or A1R can be used, and/or such one or more inhibitor(s) can be further combined with each other and/or with other therapeutic agents and/or therapies suitable for treatment of the specified disease. Two or more active agents may be co-administered to generate additive or synergistic effects. Suitable therapeutically effective dosages for each agent may be lowered due to the additive action or synergy.

For example, for treatment of tinnitus, the inhibitor(s) of Nt5e and/or A1R can be combined with the art-known tinnitus treatments such as earwax removal, treating a blood vessel condition, noise suppression (e.g., using a white noise machine), a hearing aid, masking therapy auditory exposure (e.g., using masking devices producing a continuous, low-level white noise or delivering individually programmed tonal music to mask the specific frequencies of the tinnitus), frequency discrimination training, antidepressants (e.g., amitriptyline, nortriptyline, Alprazolam [Niravam, Xanax]), anti-anxiety medications, neurostimulation techniques including transcranial magnetic stimulation and cortical stimulation, and pairing multiple tone frequencies with vagus nerve stimulation (VNS).

For example, for treatment of Williams-Beuren syndrome, the inhibitor(s) of Nt5e and/or A1R can be combined with avoidance of extra calcium and vitamin D, treating high levels of blood calcium, developmental and speech therapy, and exposure to music.

For example, for treatment of amblyopia, the inhibitor(s) of Nt5e and/or A1R can be combined with art-known treatments such as correcting the refractive error with consistent use of glasses and/or contact lenses, removing a cataract, and patching or eye drops to blur the better-seeing eye.

For example, for treatment of schizophrenia the inhibitor(s) of Nt5e and/or A1R can be combined with art-known drugs for treating schizophrenia such as, e.g., olanzapine, clozapine, haloperidol, and the like. The inhibitor(s) of Nt5e and/or A1R can be also combined with art-known antipsychotics (e.g., "typical," "atypical," and depot antipsychotics for treating schizophrenia and other psychotic conditions) and/or psychostimulants (for treating learning disorders). "Typical" antipsychotics are conventional antipsychotics such as, e.g., phenothiazine, butryophenones, thioxantheses, dibenzoxazepines, dihydroindolones, and diphenylbutylpiperidines. "Atypical" antipsychotics are a new generation of antipsychotics which generally act on the dopamine $D_2$ and $5HT_2$ serotonin receptor and have high levels of efficacy and a benign extrapyramidal symptom side effect profile. Examples of typical antipsychotics include, e.g., Chlorpromazine, Thioridazine, Mesoridazine, Fluphenazine, Perphenazine, Trifluoperazine, Thiothixene, Haloperidol, Loxapine, Molindone, Acetophenazine, Droperidol, Pimozide. Examples of atypical antipsychotics include Clozapine, Risperidone, Olanzapine, and Quetiapine. Depot antipsychotics also can be used, e.g., Haloperidol decanoate, Fluphenazine decanoate, and Fluphenazine enanthate. Additional antipsychotics include, e.g., Butaperazine, Carphenazine, Remoxipride, Piperacetazine, Sulpiride, and Ziprasidone. Psychostimulants include, e.g., Dextroamphetamine, Methamphetamine, Methylphenidate, and Pemoline.

In conjunction with the combination treatments, the invention also provides pharmaceutical compositions that contain one or more inhibitors of Nt5e and/or A1R along with one or more additional therapeutics.

Inhibitors of Nt5e or A1R Gene Expression and/or Protein Production

In conjunction with the above methods, the present invention provides inhibitors of Nt5e or A1R. In one embodiment, such inhibitors are inhibitors Nt5e or A1R gene expression and/or protein production. Non-limiting examples of such inhibitors include, e.g., interfering RNA molecules (e.g., siRNA or shRNA), dsRNA, RNA polymerase III transcribed DNAs, ribozymes, and antisense nucleic acids.

Antisense oligonucleotides, including antisense DNA, RNA, and DNA/RNA molecules, act to directly block the translation of mRNA by binding to targeted mRNA and preventing protein translation. Preferably, antisense oligonucleotides are of at least about 15 bases and are complementary to unique regions of the target DNA sequence. Such antisense oligonucleotides can be synthesized, e.g., by conventional techniques (see, e.g., Dallas et al., (2006) Med. Sci. Monit. 12(4):RA67-74; Kalota et al., (2006) Handb. Exp. Pharmacol. 173:173-96; Lutzelburger et al., (2006) Handb. Exp. Pharmacol. 173:243-59).

RNA interference (RNAi) is a process of sequence-specific post-transcriptional gene silencing by which double stranded RNA (dsRNA) homologous to a target locus can specifically inactivate gene function (Hammond et al., Nature Genet. 2001; 2:110-119; Sharp, Genes Dev. 1999; 13:139-141). This dsRNA-induced gene silencing is mediated by short double-stranded small interfering RNAs (siRNAs) generated from longer dsRNAs by ribonuclease III cleavage (Bernstein et al., Nature 2001; 409:363-366 and Elbashir et al., Genes Dev. 2001; 15:188-200). RNAi-mediated gene silencing is thought to occur via sequence-specific RNA degradation, where sequence specificity is determined by the interaction of an siRNA with its complementary sequence within a target RNA (see, e.g., Tuschl, Chem. Biochem. 2001; 2:239-245). RNAi can be activated by introduction of siRNAs (Elbashir, et al., Nature 2001; 411: 494-498) or short hairpin RNAs (shRNAs) bearing a fold back stem-loop structure (Paddison et al., Genes Dev. 2002; 16: 948-958; Sui et al., Proc. Natl. Acad. Sci. USA 2002; 99:5515-5520; Brummelkamp et al., Science 2002; 296:550-553; Paul et al., Nature Biotechnol. 2002; 20:505-508).

siRNA/shRNA comprises a double stranded structure typically containing 15 to 50 base pairs and preferably 21 to 25 base pairs and having a nucleotide sequence identical or nearly identical to an expressed target gene or RNA within the cell. The siRNA/shRNA inhibitors of the present invention are preferably short double stranded nucleic acid duplexes (or stem-loop structures in case of shRNA) comprising annealed complementary single stranded nucleic acid molecules. However, the invention also encompasses embodiments in which the siRNAs comprise an annealed RNA:DNA duplex, wherein the sense strand of the duplex is a DNA molecule and the antisense strand of the duplex is a RNA molecule. In some embodiments, duplexed siRNAs have a 2 or 3 nucleotide 3' overhang on each strand of the duplex. In some embodiments, siRNAs/shRNAs have 5'-phosphate and 3'-hydroxyl groups.

According to the present invention, siRNAs may be introduced to a target cell as an annealed duplex siRNA, or as single stranded sense and antisense nucleic acid sequences that, once within the target cell, anneal to form the siRNA duplex. Alternatively, the sense and antisense strands of the siRNA may be encoded on an expression construct that is introduced to the target cell. Upon expression within the target cell, the transcribed sense and antisense strands may anneal to reconstitute the siRNA. 100% sequence complementarity between the siRNA and the target nucleic acid is not required to practice the invention.

In one specific embodiment, the inhibitor of Nt5e is shRNA Nt5e (1264) 5'-ACATTTGACCTCGTCCAAT-TAAAAGGGTC-3' (SEQ ID NO: 12; coding DNA sequence) or shRNA Nt5e (1366) 5'-GGAATCCATGTG-GTGTACGATATTAACCG-3' (SEQ ID NO: 13; coding DNA sequence). In one specific embodiment, the inhibitor of A1R is shRNA A1R (123) 5'-CGATGCTACCTTCTGCT-TCATCGTATCCC-3' (SEQ ID NO: 10; coding DNA sequence) or shRNA A1R (789) 5'-CCAGAAACCCAG-CATCCTCATCTACATTG-3' (SEQ ID NO: 11; coding DNA sequence).

RNA polymerase III transcribed DNAs contain promoters, such as the U6 promoter. These DNAs can be transcribed to produce small hairpin RNAs in the cell that can function as siRNA or linear RNAs that can function as antisense RNA. The inhibitor may be polymerized in vitro, recombinant RNA, contain chimeric sequences, or derivatives of these groups. The inhibitor may contain ribonucleotides, deoxyribonucleotides, synthetic nucleotides, or any suitable combination such that the target RNA and/or gene is inhibited. In addition, these forms of nucleic acid may be single, double, triple, or quadruple stranded. (see for example Bass (2001) Nature, 411, 428 429; Elbashir et al., (2001) Nature, 411, 494 498; and PCT Publication Nos. WO 00/44895, WO 01/36646, WO 99/32619, WO 00/01846, WO 01/29058, WO 99/07409, WO 00/44914).

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hammerhead motif ribozyme molecules that specifically and efficiently catalyze endonucleolytic cleavage of mRNA sequences are also within the scope of the present invention. Scanning the target molecules for ribozyme cleavage sites that include the following sequences, GUA, GUU, and GUC initially identifies specific ribozyme cleavage sites within any potential RNA target. Once identified, short RNA sequences of between about 15 and 20 ribonucleotides corresponding to the region of the target gene containing the cleavage site can be evaluated for predicted structural features such as secondary structure that may render the oligonucleotide sequence unsuitable. The suitability of candidate targets can also be evaluated by testing their accessibility to hybridization with complementary oligonucleotides using, e.g., ribonuclease protection assays.

Aptamers nucleic acid sequences are readily made that bind to a wide variety of target molecules. The aptamer nucleic acid sequences useful in the methods of the invention can be comprised entirely of RNA or partially of RNA, or entirely or partially of DNA and/or other nucleotide analogs. Aptamers are typically developed to bind particular ligands by employing known in vivo or in vitro (most typically, in vitro) selection techniques known as SELEX (Systematic Evolution of Ligands by Exponential Enrichment). Methods of making aptamers are described in, for example, Ellington and Szostak (1990) Nature 346:818, Tuerk and Gold (1990) Science 249:505, U.S. Pat. No. 5,582,981; PCT Publication No. WO 00/20040; U.S. Pat. No. 5,270,163; Lorsch and Szostak (1994) Biochem. 33:973; Mannironi et al., (1997) Biochem. 36:9726; Blind (1999) Proc. Nat'l. Acad. Sci. USA 96:3606-3610; Huizenga and Szostak (1995) Biochem. 34:656-665; PCT Publication Nos. WO 99/54506, WO 99/27133, and WO 97/42317; and U.S. Pat. No. 5,756,291.

Nucleic acid-based inhibitors of the invention may include one or more modifications, e.g., to increase intracellular stability and efficacy (e.g., modifications to the base moiety, sugar moiety, phosphate moiety, phosphate-sugar backbone, or a combination thereof). For example, the phosphodiester linkages may be modified to include at least one heteroatom other than oxygen, such as nitrogen or sulfur. In this case, for example, the phosphodiester linkage may be replaced by a phosphothioester linkage. Similarly, bases may be modified to block the activity of adenosine deaminase. Other examples of useful modifications are morpholino modifications and LNA. Where the nucleic acid-based inhibitor molecule is produced synthetically, or by in vitro transcription, a modified nucleoside may be introduced during synthesis or transcription.

Non-limiting examples of modified base moieties include inosine, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

Non-limiting examples of modified sugar moieties include arabinose, 2-fluoroarabinose, xylulose, and hexose. Modified siRNAs may contain substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—; S—, or N-alkyl; O—, S—, or N-alkenyl; $SOCH_3$; $SO_2CH_3$; $ONO_2$; $NO_2$; $N_3$; $NH_2$; heterocycloalkyl; heterocloalkaryl; aminoalkylamino; polyalkylamino; substituted sialyl; a fluorescein moiety; a reporter group; a group for improving the pharmacokinetic properties; or a group for improving the pharmacodynamic properties, and other substituents having similar properties. Modified nucleic acid-based inhibitors may also have sugar mimetics such as cyclobutyls or other carbocyclics in place of the pentofuranosyl group.

Non-limiting examples of modifications of phosphate backbone include a phosphorothioate, a phosphorodithioate, a phosphoramidothioate, a phosphoramidate, a phosphordiamidate, a methylphosphonate, a phosphotriester, an alkyl phosphotriester, and a formacetal or analog thereof, as well as chimeras between methylphosphonate and phosphodiester, short chain alkyl, or cycloalkyl intersugar linkages or short chain heteroatomic or heterocyclic intersugar linkages. Specific non-limiting examples include those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—$PO_2$—O—$CH_2$). U.S. Pat. No. 5,677,437 describes heteroaromatic oligonucleoside linkages. Nitrogen linkers or groups containing nitrogen can also be used to prepare oligonucleotide mimics (U.S. Pat. Nos. 5,792,844 and 5,783,682). U.S. Pat. No. 5,637,684 describes phosphoramidate and phosphorothioamidate oligomeric compounds.

Also envisioned are modified nucleic acid-based inhibitors having morpholino backbone structures in which the bases are linked to 6-membered morpholine rings, which are connected to other morpholine-linked bases via non-ionic phosphorodiamidate intersubunit linkages. Morpholino derivatives are highly resistant to nucleases and have good targeting predictability (U.S. Pat. No. 5,034,506; Summerton, Biochim. Biophys. Acta 1999; 1489:141-158; Summerton and Weller, Antisense Nucleic Acid Drug Dev. 1997; 7:187-195; Arora et al., J. Pharmacol. Exp. Ther. 2000; 292:921-928; Qin et al., Antisense Nucleic Acid Drug Dev. 2000; 10:11-16; Heasman et al., Dev. Biol. 2000; 222:124-134; Nasevicius and Ekker, Nat. Genet. 2000; 26:216-220).

Another type of a useful modification is the peptide-nucleic acid (PNA) backbone: the phosphodiester backbone of the oligonucleotide may be replaced with a polyamide backbone, the bases being bound directly or indirectly to the aza nitrogen atoms of the polyamide backbone (Nielsen et al., Science 1991; 254:1497).

In other embodiments, locked nucleic acids (LNA) can be used (reviewed in, e.g., Jepsen and Wengel, Curr. Opin. Drug Discov. Devel. 2004; 7:188-194; Crinelli et al., Curr. Drug Targets 2004; 5:745-752). LNA are nucleic acid analog(s) with a 2'-O, 4'-C methylene bridge. This bridge restricts the flexibility of the ribofuranose ring and locks the structure into a rigid C3-endo conformation, conferring enhanced hybridization performance and exceptional biostability.

Modified nucleic acid-based inhibitors can include appending groups such as, e.g., peptides, or agents facilitating transport across the cell membrane (see, e.g., Letsinger et al., Proc. Natl. Acad. Sci. USA 1989; 86:6553-6556; Lemaitre et al., Proc. Natl. Acad. Sci. USA 1987; 84:648-652; PCT Publication No. WO 88/09810), or blood-brain barrier (see, e.g., PCT Publication No. WO 89/10134), etc.

Nucleic acid-based inhibitors of the invention can be synthesized by standard methods known in the art, e.g., by use of an automated synthesizer. In one embodiment, RNA molecules can be chemically synthesized using appropriately protected ribonucleoside phosphoramidites and a conventional DNA/RNA synthesizer. In case of siRNA molecules, following chemical synthesis, single stranded RNA molecules are deprotected, annealed to form siRNAs, and purified (e.g., by gel electrophoresis or HPLC). Commercial suppliers of synthetic RNA molecules or synthesis reagents include, e.g., Proligo (Hamburg, Germany), Dharmacon Research (Lafayette, Colo.), Pierce Chemical (part of Perbio Science, Rockford, Ill.), Glen Research (Sterling, Va.), ChemGenes (Ashland, Mass.) and Cruachem (Glasgow, UK).

Alternatively, standard procedures may be used for in vitro transcription of RNA from DNA templates carrying RNA polymerase promoter sequences (e.g., T7 or SP6 RNA polymerase promoter sequences) (Donze and Picard, Nucleic Acids Res. 2002; 30:e46; Yu et al., Proc. Natl. Acad. Sci. USA 2002; 99:6047-6052; Weintraub, H. et al., Trends in Genetics, Vol. 1 (1) 1986). In the case of siRNA molecules, the sense and antisense transcripts may be synthesized in two independent reactions and annealed later, or may be synthesized simultaneously in a single reaction. siRNA molecules may be formed within a cell by transcription of RNA from an expression construct introduced into the cell. For example, both a protocol and an expression construct for in vivo expression of siRNAs are described in Yu et al., supra.

The expression constructs for in vivo production of nucleic acid-based inhibitors of the invention comprise encoding sequences operably linked to elements necessary for the proper transcription, including promoter elements and transcription termination signals. Non-limiting examples of promoters for use in such expression constructs include the polymerase-III HI-RNA promoter (see, e.g., Brummelkamp et al., supra) and the U6 polymerase-III promoter (see, e.g., Sui et al., supra; Paul, et al. supra; and Yu et al., supra). The expression constructs can further comprise vector sequences that facilitate the cloning of the expression constructs. Standard vectors that may be used in practicing the current invention are known in the art (e.g., pSilencer 2.0-U6 vector, Ambion Inc., Austin, Tex.).

Small Molecule Inhibitors of the Invention

The present invention also encompasses various small molecule inhibitors of Nt5e or A1R gene expression and/or protein function. Small molecules are a diverse group of synthetic and natural substances generally having low molecular weights (preferably less than about 2000 Daltons, less than about 1000 Daltons, or less than about 500 Daltons). Small molecules, without limitation, may be, for example, nucleic acids, peptides, polypeptides, peptide nucleic acids, peptidomimetics, carbohydrates, lipids, or other organic (carbon containing) or inorganic molecules and may be synthetic or naturally occurring or optionally derivatized. Such small molecules may be a therapeutically deliverable substance or may be further derivatized to facilitate delivery or targeting.

In one embodiment, the inhibitors of the invention are compounds having a structure according to Formula I:

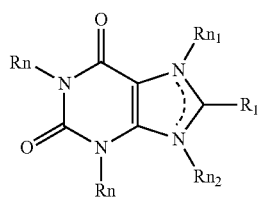

(I)

wherein $R_1$ is selected from hydrogen, —F; —Cl; —Br; —I; —OH, —OR*; —NH$_2$; —NHR*; —N(R*)$_2$; —N(R*)$_3^+$; —SH; —SR*; —CN; —NC; —(C=O)—R*; —CHO; —CO$_2$H; —CO$_2$; —CO$_2$R*; —(C=O)—S—R*; —O—(C=O)—H; —O—(C=O)—R*; —S—(C=O)— R*; —(C=O)—NH$_2$; —(C=O)—N(R*)$_2$; —SCN; —NCS; —NSO; —SO$_2$—R*; —O—S(=O)$_2$—R*; —S(=O)$_2$—OR*; —N$_2$—R*; —N(C$_2$H$_4$); —Si(R*)$_3$; —CF$_3$; —O—CF$_3$; —PR*$_2$; —O—P(=O)(OR*)$_2$; —P(=O)(OR*)$_2$; perfluoroalkyl; an aliphatic $C_1$-$C_{20}$ hydrocarbon radical; a $C_1$-$C_{12}$ aromatic hydrocarbon radical; or a $C_1$-$C_{12}$ heteroaryl radical; where R* is independently at each occurrence hydrogen or a straight chained, branched, or cyclic $C_1$-$C_{20}$ hydrocarbon radical, which may be saturated, partially saturated, or aromatic, each of which may be optionally substituted with 1-6 heteroatoms selected from nitrogen, oxygen, sulfur, phosphorus, or halogen;

$R_n$ is independently at each occurrence selected from hydrogen or a straight chained, branched, or cyclic saturated, partially saturated, or aromatic $C_1$-$C_{20}$ hydrocarbon radical, optionally substituted with 1-12 heteroatoms selected from nitrogen, oxygen, sulfur, phosphorus, or halogen;

$Rn_1$ is selected from $R_n$ or, if $Rn_2$ is present, $Rn_1$ is a bond, i.e. $Rn_1$ is altogether absent; and $Rn_2$ is selected from $R_n$ or, if $Rn_1$ is present, $Rn_2$ is a bond, i.e. $Rn_2$ is altogether absent; and pharmaceutically acceptable salts thereof.

In some embodiments of the compounds of Formula I, $R_1$ is hydrogen or a straight chained, branched, or cyclic saturated, partially saturated, or aromatic $C_1$-$C_{16}$ hydrocarbon radical (e.g., methyl, ethyl, propyl, isopropyl, cyclopentyl, phenyl, benzyl, etc.), or a saturated, partially saturated, or aromatic $C_1$-$C_{12}$ hydrocarbon radical, or a saturated, partially saturated, or aromatic $C_1$-$C_{10}$ hydrocarbon radical, or a saturated, partially saturated, or aromatic $C_1$-$C_8$ hydrocarbon radical, optionally substituted with 1-6 heteroatoms selected from nitrogen, oxygen, sulfur, phosphorus, or halogen. In some embodiments of the compounds of Formula I, $R_1$ is selected from cyclopentyl, cyclohexyl, cyclooctyl, bridged cyclooctyl, adamantyl, benzyl, or phenyl, optionally substituted with a straight chained, branched, or cyclic $C_1$-$C_{12}$ hydrocarbon radical, which may be saturated, partially saturated, or aromatic, each of which may be optionally substituted with 1-6 heteroatoms selected from nitrogen, oxygen, sulfur, phosphorus, or halogen.

In some embodiments of the compounds of Formula I, Rn is hydrogen or a straight chained, branched, or cyclic saturated, partially saturated, or aromatic $C_1$-$C_{16}$ hydrocarbon radical (e.g., methyl, ethyl, propyl, isopropyl, etc.), or a straight chained, branched, or cyclic saturated, partially saturated, or aromatic $C_1$-$C_{12}$ hydrocarbon radical, or a straight chained, branched, or cyclic saturated, partially saturated, or aromatic $C_1$-$C_{10}$ hydrocarbon radical, or a straight chained, branched, or cyclic saturated, partially saturated, or aromatic $C_1$-$C_8$ hydrocarbon radical, or a straight chained, branched, or cyclic saturated, partially saturated, or aromatic $C_1$-$C_6$ hydrocarbon radical, optionally substituted with 1-6 heteroatoms selected from nitrogen, oxygen, sulfur, or halogen. In some embodiments of the compounds of Formula I, Rn is hydrogen, methy, ethyl, propyl, or butyl. In some embodiments of the compounds of Formula I, Rn is (CH$_2$)$_3$—OH or (CH$_2$)$_2$—NR*, where R* is as defined above.

In one embodiment according to Formula I, the compounds have a structure according to Formula Ia:

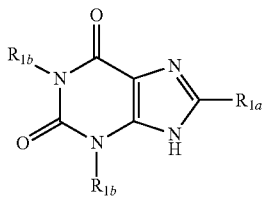

(Ia)

wherein $R_{1a}$ is selected from hydrogen, an aliphatic $C_1$-$C_{20}$ hydrocarbon radical; a $C_1$-$C_{12}$ aromatic hydrocarbon radical; or a $C_1$-$C_{12}$ heteroaryl radical, or a combination thereof; and $R_{1b'}$ is independently at each occurrence selected from hydrogen; —F; —Cl; —Br; —I; —OH, —OR*; —NH$_2$; —NHR*; —N(R*)$_2$; a straight chained, branched, or cyclic saturated, partially saturated, or aromatic $C_1$-$C_{16}$ hydrocarbon radical (e.g., methyl, ethyl, propyl, isopropyl, etc.), where R* is independently at each occurrence hydrogen or a straight chained, branched, or cyclic $C_1$-$C_{20}$ hydrocarbon radical, which may be saturated, partially saturated, or aromatic, each of which may be optionally substituted with 1-6 heteroatoms selected from nitrogen, oxygen, sulfur, phosphorus, or halogen;

and pharmaceutically acceptable salts thereof.

In another embodiment according to Formula I, the compounds have a structure according to Formula Ib.

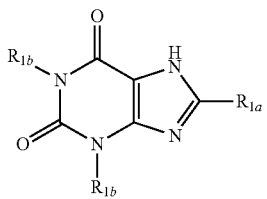

(Ib)

wherein $R_{1a}$ and $R_{1b}$ are as defined above for Formula Ia, and pharmaceutically acceptable salts thereof.

In some embodiments, the compounds have a structure according to Formulas Ic-Ir:

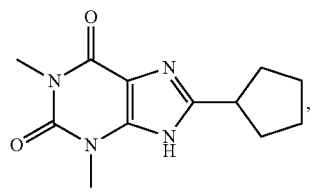

(Ic, also known as CPX, or 8-Cyclopentyl-1,3-dimethylxanthine, or 8-cyclopentyltheophylline)

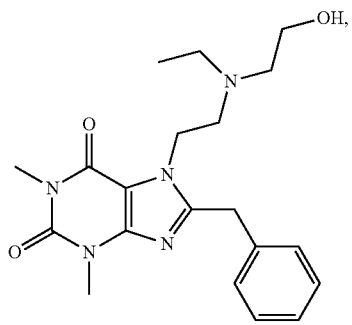

(Id, also known as Bamifylline)

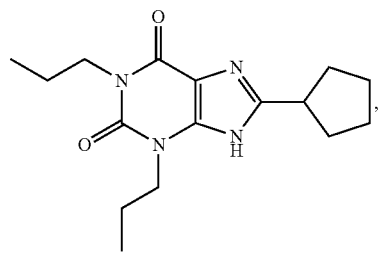

(Ie, also known as DPCPX or 8-Cyclopentyl-1,3-dipropylxanthine)

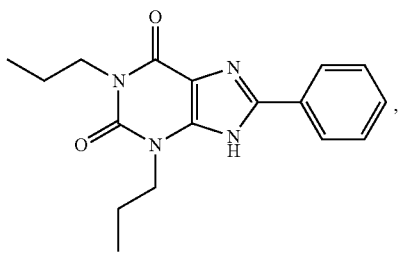

(If, also known as 1,3-Dipropyl-8-phenylxanthine)

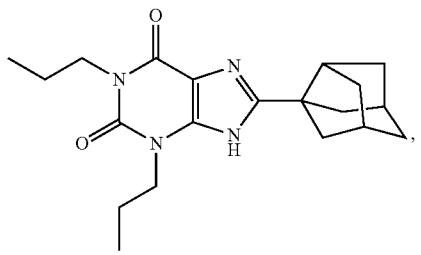

(Ig, also known as KW 3902 or Rolofylline)

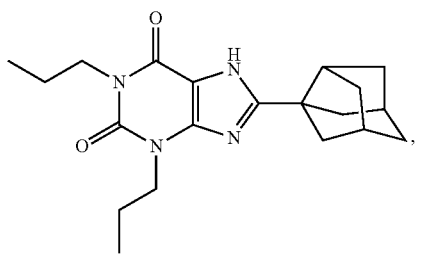

(Ih, also known as KW 3902 or Rolofylline)

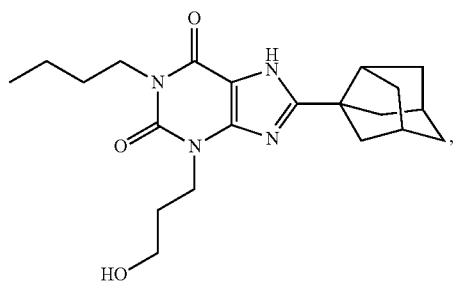

(Ii, also known as PSB 36)

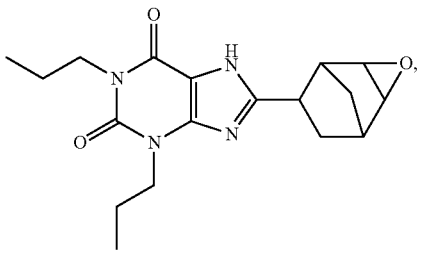

(Ij, also known as BG-9719 or Naxifylline)

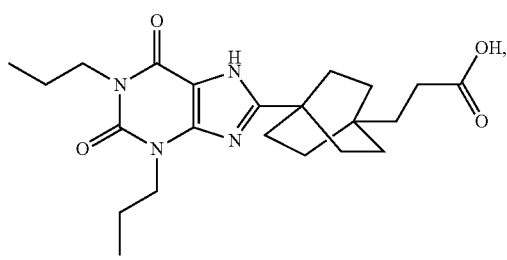

(Ik, also known as BG9928 or tonapofylline)

-continued

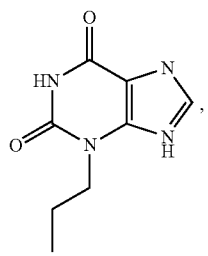

(Il, also known as Enprofylline)

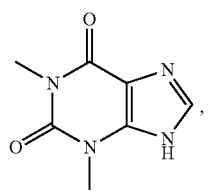

(Im, also known as Theophylline)

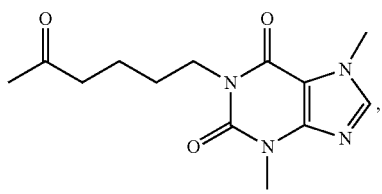

(In, also known as Pentoxyifylline)

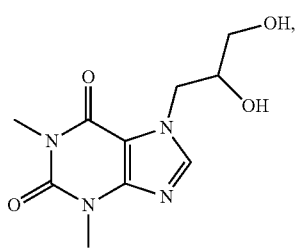

(Io, also known as Dyphylline)

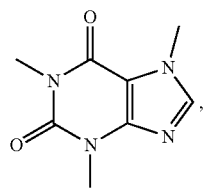

(Ip, also known as Caffeine)

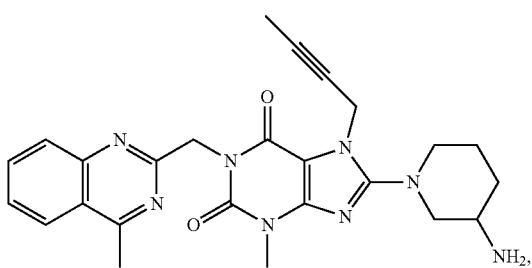

(Iq, also known as Linagliptin or BI-1356)

-continued

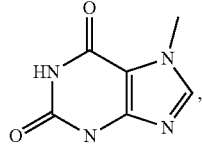

(Ir, also known as Theobromine or Xantheose)

and pharmaceutically acceptable salts thereof.

In another embodiment, the inhibitors of the invention are compounds having a structure according to Formula II:

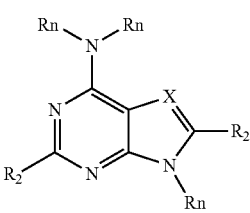

(II)

wherein X is selected from CH or N;
$R_2$ is independently at each occurrence selected from hydrogen, —F; —Cl; —Br; —I; —OH, —OR*; —NH$_2$; —NHR*; —N(R*)$_2$; —N(R*)$_3^+$; —SH; —SR*; —CN; —NC; —(C=O)—R*; —CHO; —CO$_2$H; —CO$_2$; —CO$_2$R*; —(C=O)—S—R*; —O—(C=O)—H; —O—(C=O)—R*; —S—(C=O)— R*; —(C=O)—NH$_2$; —(C=O)—N(R*)$_2$; —SCN; —NCS: —NSO; —SO$_2$R*; —O—S(=O)$_2$—R*; —S(=O)$_2$—OR*; —N2-R*; —N(C$_2$H$_4$); —Si(R*)$_3$; —CF$_3$; —O—CF$_3$; —PR*$_2$; —O—P(=O)(OR*)$_2$; —P(=O)(OR*)$_2$; perfluoroalkyl; an aliphatic C$_1$-C$_{20}$ hydrocarbon radical; a C$_1$-C$_{12}$ aromatic hydrocarbon radical; or a C$_1$-C$_{12}$ heteroaryl radical; where R* is independently at each occurrence hydrogen or a straight chained, branched, or cyclic C$_1$-C$_{20}$ hydrocarbon radical, which may be saturated, partially saturated, or aromatic, each of which may be optionally substituted with 1-6 heteroatoms selected from nitrogen, oxygen, sulfur, phosphorus, or halogen;
Rn is selected from hydrogen or a straight chained, branched, or cyclic saturated, partially saturated, or aromatic C$_1$-C$_{20}$ hydrocarbon radical, or a C$_1$-C$_{20}$ carbohydrate, optionally substituted with 1-12 heteroatoms selected from nitrogen, oxygen, sulfur, phosphorus, or halogen;
and pharmaceutically acceptable salts thereof.

In some implementations of the compounds of Formula II, $R_2$ is hydrogen or a straight chained, branched, or cyclic saturated, partially saturated, or aromatic C$_1$-C$_{16}$ hydrocarbon radical, optionally substituted with 1-6 heteroatoms selected from nitrogen, oxygen, sulfur, or halogen. In some implementations of the compounds of Formula II, $R_2$ is hydrogen or an aliphatic or aromatic C$_1$-C$_{16}$ hydrocarbon radical.

In some implementations of the compounds of Formula II, Rn is hydrogen or a straight chained, branched, or cyclic saturated, partially saturated, or aromatic C$_1$-C$_{16}$ hydrocarbon radical (e.g., methyl, ethyl, propyl, isopropyl, etc.), or a straight chained, branched, or cyclic saturated, partially saturated, or aromatic C$_1$-C$_{12}$ hydrocarbon radical, or a straight chained, branched, or cyclic saturated, partially saturated, or aromatic C$_1$-C$_{10}$ hydrocarbon radical, or a straight chained, branched, or cyclic saturated, partially saturated, or aromatic $C_1$-$C_8$ hydrocarbon radical, or a straight chained, branched, or cyclic saturated, partially saturated, or aromatic $C_1$-$C_6$ hydrocarbon radical, optionally substituted with 1-6 heteroatoms selected from nitrogen, oxygen, sulfur, or halogen. In some implementations, Rn is hydrogen. In other implementations, Rn is a $C_1$-$C_{16}$ carbohydrate, optionally substituted with one or more straight chained, branched, or cyclic $C_1$-$C_{20}$ hydrocarbon radical, or 1-12 heteroatoms selected from nitrogen, oxygen, sulfur, phosphorus, or halogen; and pharmaceutically acceptable salts thereof.

In some embodiments according to Formula II, the compounds have a structure according to Formulas IIa-IIb:

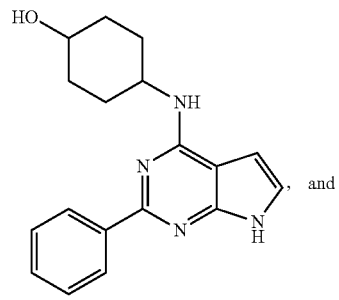

(IIa, also known as SLV 320)

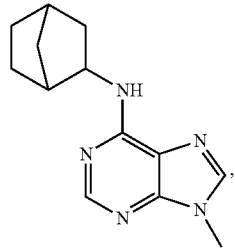

(IIb, also known as N 0861)

and pharmaceutically acceptable salts thereof.

In another embodiment, the compounds have a structure according to Formulas IIc-IIe:

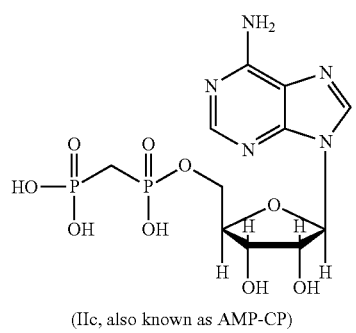

(IIc, also known as AMP-CP)

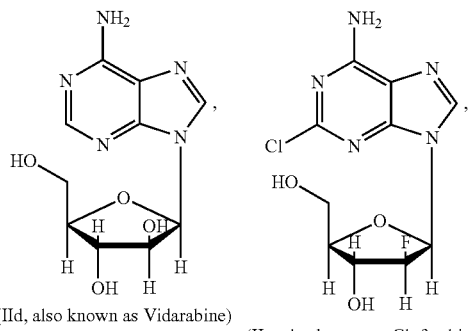

(IId, also known as Vidarabine)

(IIe, also known as Clofarabine)

and pharmaceutically acceptable salts thereof. In yet another embodiment, the inhibitors of the invention are compounds having a structure according to Formula III:

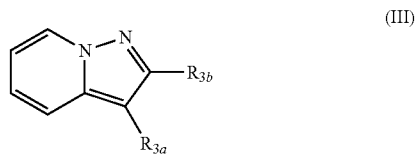

(III)

wherein $R_{3a}$ and $R_{3b}$ are independently selected from hydrogen, —F; —Cl; —Br; —I; —OH, —OR*; —NH$_2$; —NHR*; —N(R*)$_2$; —N(R*)$_3^+$; —SH; —SR*; —CN; —NC; —(C=O)—R*; —CHO; —CO$_2$H; —CO$_2$; —CO$_2$R*; —(C=O)—S—R*; —O—(C=O)—H; —O—(C=O)—R*; —S—(C=O)— R*; —(C=O)—NH$_2$; —(C=O)—N(R*)$_2$; —SCN; —NCS; —NSO; —SO$_2$—R*; —O—S(=O)$_2$—R*; —S(=O)$_2$—OR*; —N$_2$—R*; —N(C$_2$H$_4$); —Si(R*)$_3$; —CF$_3$; —O—CF$_3$; —PR*$_2$; —O—P(=O)(OR*)$_2$; —P(=O)(OR*)$_2$; perfluoroalkyl; an aliphatic $C_1$-$C_{20}$ hydrocarbon radical; a $C_1$-$C_{12}$ aromatic hydrocarbon radical; or a $C_1$-$C_{12}$ heteroaryl radical, or combinations thereof; where R* is independently at each occurrence hydrogen or a straight chained, branched, or cyclic $C_1$-$C_{20}$ hydrocarbon radical, which may be saturated, partially saturated, or aromatic, each of which may be optionally substituted with 1-6 heteroatoms selected from nitrogen, oxygen, sulfur, phosphorus, or halogen;

and pharmaceutically acceptable salts thereof. In some implementations of the compounds of Formula II, $R_{3a}$ and $R_{3b}$ are independently hydrogen or a straight chained, branched, or cyclic saturated, partially saturated, or aromatic $C_1$-$C_{16}$ hydrocarbon radical, or a saturated, partially saturated, or aromatic $C_1$-$C_{12}$ hydrocarbon radical, or a saturated, partially saturated, or aromatic $C_1$-$C_{10}$ hydrocarbon radical, or a saturated, partially saturated, or aromatic $C_1$-$C_8$ hydrocarbon radical, or a saturated, partially saturated, or aromatic $C_1$-$C_6$ hydrocarbon radical, or combinations thereof, optionally substituted with 1-6 heteroatoms selected from nitrogen, oxygen, sulfur, or halogen. In some embodiments of the compounds of Formula III, $R_{3b}$ is phenyl.

In one embodiment according to Formula III, the compounds have a structure according to Formula IIIa:

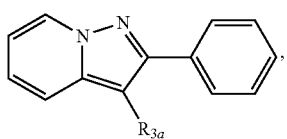

(IIIa)

wherein $R_{3a}$ is selected from hydrogen, acyl, or a $C_1$-$C_{20}$ hydrocarbon radical, which may be saturated, partially saturated, or aromatic, each of which may be optionally substituted with 1-6 heteroatoms selected from nitrogen, oxygen, sulfur, phosphorus, or halogen.

In other embodiments according to Formula III, the compounds have a structure according to Formulas IIIb-IIIh:

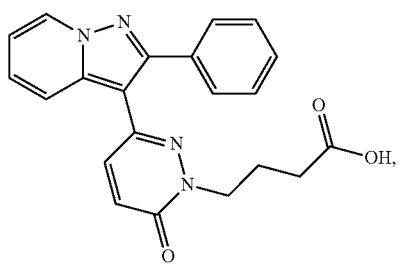

(IIIb, also known as FK-838)

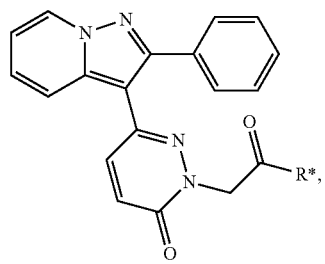

(IIIc)

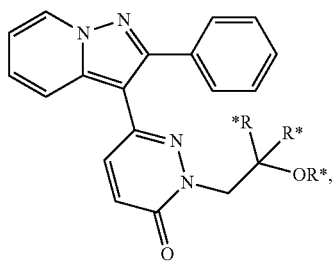

(IIId)

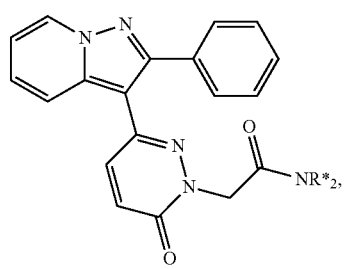

(IIIe)

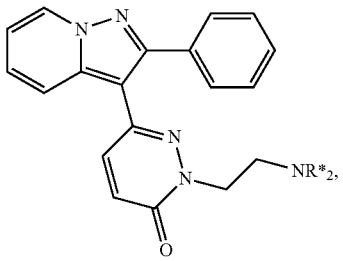

(IIIf)

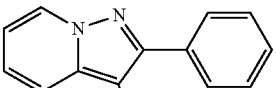

(IIIg)

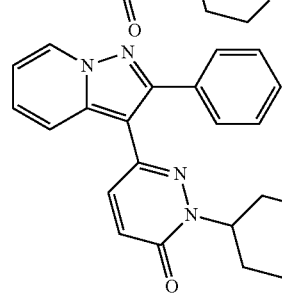

(IIIh, also known as FR194921)

wherein R* is independently at each occurrence hydrogen or a straight chained, branched, or cyclic $C_1$-$C_{20}$ hydrocarbon radical, which may be saturated, partially saturated, or aromatic, each of which may be optionally substituted with 1-6 heteroatoms selected from nitrogen, oxygen, sulfur, phosphorus, or halogen. In some embodiments, two R* groups located on the same atom may fuse together to form a $C_1$-$C_8$ ring; and pharmaceutically acceptable salts thereof.

In some embodiments of the compounds of Formulas IIIc-IIIg, R* is independently at each occurrence selected from hydrogen, or a straight chained, branched, or cyclic saturated, partially saturated, or aromatic $C_1$-$C_{16}$ hydrocarbon radical (e.g., methyl, ethyl, propyl, isopropyl, etc.).

In another embodiment according to Formula III, the compound has a structure according to Formula IIIi:

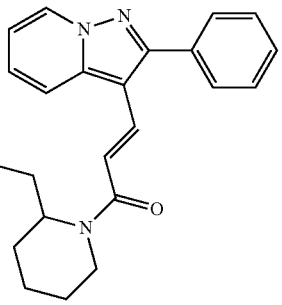

(IIIi, also known as FK-453)

and pharmaceutically acceptable salts thereof.

In yet another embodiment, the inhibitors of the invention are compounds having a structure according to Formula IV:

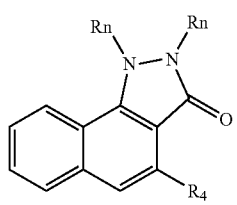

(IV)

wherein $R_4$ is selected from hydrogen, —F; —Cl; —Br; —I; —OH, —OR*; —NH$_2$; —NHR*; —N(R*)$_2$; —N(R*)$_3^+$; —SH; —SR*; —CN; —NC; —(C=O)—R*; —CHO; —CO$_2$H; —CO$_2$; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —SCN; —NCS; —NSO; —SO$_2$—R*; —O—S(=O)$_2$—R*; —S(=O)$_2$—OR*; —N$_2$—R*; —N(C$_2$H$_4$); —Si(R*)$_3$; —CF$_3$; —O—CF$_3$; —PR*$_2$; —O—P(=O)(OR*)$_2$; —P(=O)(OR*)$_2$; perfluoroalkyl; an aliphatic $C_1$-$C_{20}$ hydrocarbon radical; a $C_1$-$C_{12}$ aromatic hydrocarbon radical; or a $C_1$-$C_{12}$ heteroaryl radical; where R* is independently at each occurrence hydrogen or a straight chained, branched, or cyclic $C_1$-$C_{20}$ hydrocarbon radical, which may be saturated, partially saturated, or aromatic, each of which may be optionally substituted with 1-6 heteroatoms selected from nitrogen, oxygen, sulfur, phosphorus, or halogen;
$R_n$ is independently at each occurrence selected from hydrogen or a straight chained, branched, or cyclic saturated, partially saturated, or aromatic $C_1$-$C_{20}$ hydrocarbon radical, optionally substituted with 1-12 heteroatoms selected from nitrogen, oxygen, sulfur, phosphorus, or halogen;
and pharmaceutically acceptable salts thereof.

In one embodiment according to Formula IV, the compounds have a structure according to Formula IVa:

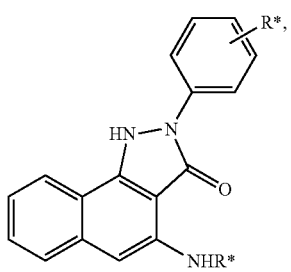

(IVa)

wherein R* is independently at each occurrence hydrogen, halogen, or a straight chained, branched, or cyclic $C_1$-$C_{20}$ hydrocarbon radical, which may be saturated, partially saturated, or aromatic, each of which may be optionally substituted with 1-6 heteroatoms selected from nitrogen, oxygen, sulfur, phosphorus, or halogen. In some embodiments, R* is a straight chained, branched, or cyclic saturated, partially saturated, or aromatic $C_1$-$C_{16}$ hydrocarbon radical (e.g., methyl, ethyl, propyl, isopropyl, etc.). In some other embodiments, R* is a halogen.

In one particular implementation of the compounds according to Formula IV, the compound has a structure according to Formula IVb:

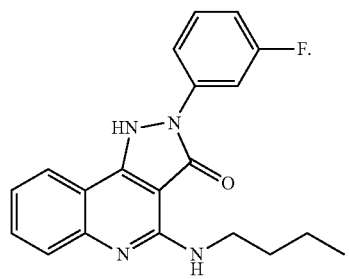

(IVb, also known as PQ-69)

In one embodiment, the inhibitor is a compound selected from the group consisting of Azelastine, Tetrahydrobiopterin, Silodosin, Pefloxacin, Folic acid, Pomalidomide, Mefloquine, Letrozole, Pemetrexed, Droperidol, and Ticagrelor, and pharmaceutically acceptable derivatives and salts thereof.

The above compounds may be obtained by methods known to skilled practitioners. Syntheses, characterization, and biological activity data for some of these compounds are disclosed in, e.g., Scifinder, Chem. Pharm. Bull. 49(8) 988-998 (2001); J Pharmacol Sci 96, 42-52 (2004).

Additional small molecule inhibitors of Nt5e or A1R can be isolated from natural sources (for example, plants, fungi, microbes and the like) or isolated from random or combinatorial chemical libraries of synthetic or natural compounds, or synthesized. See Werner et al., (2006) Brief Funct. Genomic Proteomic 5(1):32-6. Many random or combinatorial libraries are known in the art that can be used. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from, e.g., Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., (1996) Tib Tech 14:60).

Methods for preparing libraries of molecules are well known in the art and many libraries are commercially available. Libraries of interest in the invention include peptide libraries, randomized oligonucleotide libraries, synthetic organic combinatorial libraries, and the like. Degenerate peptide libraries can be readily prepared in solution, in immobilized form as bacterial flagella peptide display libraries or as phage display libraries. Peptide ligands can be selected from combinatorial libraries of peptides containing at least one amino acid. Libraries can be synthesized of peptoids and non-peptide synthetic moieties. Such libraries can further be synthesized which contain non-peptide synthetic moieties, which are less subject to enzymatic degradation compared to their naturally-occurring counterparts. Libraries are also meant to include for example but are not limited to peptide-on-plasmid libraries, polysome libraries, aptamer libraries, synthetic peptide libraries, synthetic small molecule libraries and chemical libraries. The libraries can also comprise cyclic carbon or heterocyclic structure and/or aromatic or polyaromatic structures substituted with one or more of the above-identified functional groups.

Examples of chemically synthesized libraries are described in Fodor et al., (1991) Science 251:767-773; Houghten et al., (1991) Nature 354:84-86; Lam et al., (1991) Nature 354:82-84; Medynski, (1994) BioTechnology 12:709-710; Gallop et al., (1994) J. Medicinal Chemistry 37(9):1233-1251; Ohlmeyer et al., (1993) Proc. Natl. Acad. Sci. USA 90:10922-10926; Erb et al., (1994) Proc. Natl. Acad. Sci. USA 91:11422-11426; Houghten et al., (1992) Biotechniques 13:412; Jayawickreme et al., (1994) Proc. Natl. Acad. Sci. USA 91:1614-1618; Salmon et al., (1993) Proc. Natl. Acad. Sci. USA 90:11708-11712; PCT Publication No. WO 93/20242, dated Oct. 14, 1993; and Brenner et al., (1992) Proc. Natl. Acad. Sci. USA 89:5381-5383.

Examples of phage display libraries are described in Scott et al., (1990) Science 249:386-390; Devlin et al., (1990) Science, 249:404-406; Christian, et al., (1992) J. Mol. Biol. 227:711-718; Lenstra, (1992) J. Immunol. Meth. 152:149-157; Kay et al., (1993) Gene 128:59-65; and PCT Publication No. WO 94/18318.

Screening the libraries can be accomplished by any variety of commonly known methods. See, for example, the following references, which disclose screening of peptide libraries: Parmley and Smith, (1989) Adv. Exp. Med. Biol. 251:215-218; Scott and Smith, (1990) Science 249:386-390; Fowlkes et al., (1992) BioTechniques 13:422-427; Oldenburg et al., (1992) Proc. Natl. Acad. Sci. USA 89:5393-5397; Yu et al., (1994) Cell 76:933-945; Staudt et al., (1988) Science 241:577-580; Bock et al., (1992) Nature 355:564-566; Tuerk et al., (1992) Proc. Natl. Acad. Sci. USA 89:6988-6992; Ellington et al., (1992) Nature 355:850-852; U.S. Pat. Nos. 5,096,815; 5,223,409; and 5,198,346, all to Ladner et al.; Rebar et al., (1993) Science 263:671-673; and PCT Pub. WO 94/18318.

Identification and screening of inhibitors of Nt5e or A1R can be further facilitated by X-ray crystallography, neutron diffraction, nuclear magnetic resonance spectrometry, and other techniques for structure determination. These techniques provide for the rational design or identification of inhibitors.

Compositions and Methods of Administration

For enhancement of learning and memory and therapeutic applications, the Nt5e or A1R inhibitors of the present invention can be used as pharmaceutical compositions and can be optionally combined with other Nt5e and/or A1R inhibitors of the invention or other therapeutic molecules and/or treatments.

In some embodiments, the at least one inhibitor of Nt5e or A1R is formulated into a suitable pharmaceutical preparation such as, e.g., solution, suspension, tablet, dispersible tablet, pill, capsule, powder, sustained release formulation or elixir, for oral administration; sterile solution or suspension for parenteral administration; powdered or liquid spray, nose drops, a gel or ointment for intranasal administration; powdered or liquid spray for administration by inhalation; films for sublingual administration; patch for transdermal administration, etc. An inhibitor of Nt5e or A1R can be formulated into pharmaceutical compositions using any of the techniques and procedures known in the art (see, e.g., Ansel Introduction to Pharmaceutical Dosage Forms, Fourth Edition 1985, 126).

In the compositions, effective concentrations of one or more inhibitors of Nt5e and/or A1R or pharmaceutically acceptable derivatives thereof is (are) mixed with a suitable pharmaceutical carrier or vehicle.

Pharmaceutically acceptable derivatives include acids, bases, enol ethers and esters, salts, esters, hydrates, solvates and prodrug forms. A suitable derivative is selected such that its pharmacokinetic properties are superior with respect to at least one characteristic to the corresponding parent agent. The inhibitor of Nt5e or A1R may be derivatized prior to formulation.

The amount of the inhibitor of Nt5e or A1R administered and the regimen of administration will depend on absorption, inactivation and excretion rates of the active agent, the physicochemical characteristics of the agent, the severity of the condition to be alleviated, the age, condition, body weight, sex and diet of the patient, the disease state, other medications administered, and other factors known to those of skill in the art. An effective amount to treat the disease would broadly range (e.g., between about 0.001 mg and about 2000 mg per kg body weight of the recipient per day), and may be administered as a single dose or divided doses.

It is to be further understood that for any particular subject, specific dosage regimens should be adjusted over time according to the individual need and the professional judgment of the person administering or supervising the administration of the compositions.

The compositions are intended to be administered by a suitable route, including by way of example and without limitation orally, parenterally (e.g., intravenously, subcutaneously, intramuscularly), intranasally, by inhalation, sublingually, and topically. The compositions are in liquid, semi-liquid or solid form and are formulated in a manner suitable for each route of administration.

Solutions or suspensions can include any of the following components, in any combination: a sterile diluent, including by way of example without limitation, water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose.

In instances in which the agents exhibit insufficient solubility, methods for solubilizing agents may be used. Such methods are known to those of skill in this art, and include, but are not limited to, using co-solvents, such as, e.g., dimethylsulfoxide (DMSO), using surfactants, such as TWEEN®80, or dissolution in aqueous sodium bicarbonate. Pharmaceutically acceptable derivatives of the agents may also be used in formulating effective pharmaceutical compositions.

The composition can contain along with the active agent, for example and without limitation: a diluent such as lactose, sucrose, dicalcium phosphate, or carboxymethylcellulose; a lubricant, such as magnesium stearate, calcium stearate and talc; and a binder such as starch, natural gums, such as gum acacia gelatin, glucose, molasses, polyvinylpyrrolidone, celluloses and derivatives thereof, povidone, crospovidones and other such binders known to those of skill in the art. Liquid pharmaceutically administrable compositions can, for example, be prepared by dissolving, dispersing, or otherwise mixing an active agent as defined above and optional pharmaceutical adjuvants in a carrier, such as, by way of example and without limitation, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, such as, by way of example and without limitation, acetate, sodium citrate, cyclodextrin derivatives, sorbitan monolaurate, triethanolamine sodium acetate, triethanolamine oleate, and other such agents. Actual methods of preparing such dosage forms are known, or will be apparent, to those skilled in this art (e.g., Remington's Pharmaceutical Sciences, Mack Publishing Company, Easton, Pa., 15th Edition, 1975). The composition or formulation to be administered will, in any event, contain a quantity of the active agent in an amount sufficient to alleviate the symptoms of the treated subject.

The active agents or pharmaceutically acceptable derivatives may be prepared with carriers that protect the agent against rapid elimination from the body, such as time release formulations or coatings. The compositions may include other active agents to obtain desired combinations of properties.

Oral pharmaceutical dosage forms include, by way of example and without limitation, solid, gel and liquid. Solid dosage forms include tablets, capsules, granules, and bulk powders. Oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or agents of a similar nature: a binder; a diluent; a disintegrating agent; a lubricant; a glidant; a sweetening agent; and a flavoring agent.

Examples of binders include, by way of example and without limitation, microcrystalline cellulose, gum tragacanth, glucose solution, acacia mucilage, gelatin solution, sucrose, and starch paste. Lubricants include, by way of example and without limitation, talc, starch, magnesium or calcium stearate, lycopodium and stearic acid. Diluents include, by way of example and without limitation, lactose, sucrose, starch, kaolin, salt, mannitol, and dicalcium phosphate. Glidants include, by way of example and without limitation, colloidal silicon dioxide. Disintegrating agents include, by way of example and without limitation, crosscarmellose sodium, sodium starch glycolate, alginic acid, corn starch, potato starch, bentonite, methylcellulose, agar and carboxymethylcellulose. Coloring agents include, by way of example and without limitation, any of the approved certified water soluble FD and C dyes, mixtures thereof, and water insoluble FD and C dyes suspended on alumina hydrate. Sweetening agents include, by way of example and without limitation, sucrose, lactose, mannitol and artificial sweetening agents such as saccharin, and any number of spray dried flavors. Flavoring agents include, by way of example and without limitation, natural flavors extracted from plants such as fruits and synthetic blends of agents which produce a pleasant sensation, such as, but not limited to peppermint and methyl salicylate. Wetting agents include, by way of example and without limitation, propylene glycol monostearate, sorbitan monooleate, diethylene glycol monolaurate, and polyoxyethylene laural ether. Emetic-coatings include, by way of example and without limitation, fatty acids, fats, waxes, shellac, ammoniated shellac and cellulose acetate phthalates. Film coatings include, by way of example and without limitation, hydroxyethylcellulose, sodium carboxymethylcellulose, polyethylene glycol 4000 and cellulose acetate phthalate.

If oral administration is desired, the agent could be provided in a composition that protects it from the acidic environment of the stomach. For example, the composition can be formulated in an enteric coating that maintains its integrity in the stomach and releases the active agent in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The agents can also be administered as a component of an elixir, suspension, syrup, wafer, sprinkle, chewing gum or the like. A syrup may contain, in addition to the active agents, sucrose as a sweetening agent and certain preservatives, dyes and colorings and flavors. The active materials can also be mixed with other active materials which do not impair the desired action, or with materials that supplement the desired action, such as antacids, H2 blockers, and diuretics.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents may be used in any of the above dosage forms.

Solvents include, by way of example and without limitation, glycerin, sorbitol, ethyl alcohol and syrup. Examples of preservatives include, without limitation, glycerin, methyl and propylparaben, benzoic acid, sodium benzoate and alcohol. Non-aqueous liquids utilized in emulsions include, by way of example and without limitation, mineral oil and cottonseed oil. Emulsifying agents include, by way of example and without limitation, gelatin, acacia, tragacanth, bentonite, and surfactants such as polyoxyethylene sorbitan monooleate. Suspending agents include, by way of example and without limitation, sodium carboxymethylcellulose, pectin, tragacanth, Veegum and acacia. Diluents include, by way of example and without limitation, lactose and sucrose. Sweetening agents include, by way of example and without limitation, sucrose, syrups, glycerin and artificial sweetening agents such as saccharin. Wetting agents include, by way of example and without limitation, propylene glycol monostearate, sorbitan monooleate, diethylene glycol monolaurate, and polyoxyethylene lauryl ether. Organic acids include, by way of example and without limitation, citric and tartaric acid. Sources of carbon dioxide include, by way of example and without limitation, sodium bicarbonate and sodium carbonate. Coloring agents include, by way of example and without limitation, any of the approved certified water soluble FD and C dyes, and mixtures thereof. Flavoring agents include, by way of example and without limitation, natural flavors extracted from plants such fruits, and synthetic blends of agents which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245, 4,409,239, and 4,410,545. For a liquid dosage form, the solution (e.g., in a polyethylene glycol) may be diluted with a sufficient quantity of a pharmaceutically acceptable liquid carrier (e.g., water) to be easily measured for administration.

Alternatively, liquid or semi-solid oral formulations may be prepared by dissolving or dispersing the active agent or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. RE28819 and U.S. Pat. No. 4,358,603. Briefly, such formulations include, but are not limited to, those containing an agent provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Tablets and capsules formulations may be coated as known by those of skill in the art in order to modify or sustain dissolution of the active ingredient. Thus, for example and without limitation, they may be coated with a conventional enterically digestible coating, such as phenylsalicylate, waxes and cellulose acetate phthalate.

Parenteral administration, generally characterized by injection, either subcutaneously, intramuscularly or intravenously, is also contemplated herein. Injectables can be prepared in conventional forms, either as liquid solutions or suspensions, solid forms suitable for solution or suspension in liquid prior to injection, or as emulsions. Suitable excipients include, by way of example and without limitation, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as, for example, sodium acetate, sorbitan monolaurate, triethanolamine oleate and cyclodextrins.

Implantation of a slow-release or sustained-release system, such that a constant level of dosage is maintained (e.g., U.S. Pat. No. 3,710,795) is also contemplated herein. Briefly, an inhibitor of Nt5e or A1R is dispersed in a solid inner matrix (e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate) that is surrounded by an outer polymeric membrane (e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer) that is insoluble in body fluids. The agent diffuses through the outer polymeric membrane in a release rate controlling step. The percentage of active agent contained in such parenteral compositions is highly dependent on the specific nature thereof, as well as the activity of the agent and the needs of the subject.

Lyophilized powders can be reconstituted for administration as solutions, emulsions, and other mixtures or formulated as solids or gels. The sterile, lyophilized powder is prepared by dissolving an agent provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization.

Each vial will contain, by way of example and without limitation, a single dosage (10-1000 mg, such as 100-500 mg) or multiple dosages of the agent. The lyophilized powder can be stored under appropriate conditions, such as at about 4° C. to room temperature. Reconstitution of this lyophilized powder with water for injection provides a formulation for use in parenteral administration. For reconstitution, about 1-50 mg, such as about 5-35 mg, for example, about 9-30 mg of lyophilized powder, is added per mL of sterile water or other suitable carrier. The precise amount depends upon the selected agent. Such amount can be empirically determined.

The inhibitors of Nt5e or A1R or pharmaceutically acceptable derivatives thereof may be formulated as aerosols for application e.g., by inhalation or intranasally (e.g., as described in U.S. Pat. Nos. 4,044,126, 4,414,209, and 4,364,923). These formulations can be in the form of an aerosol or solution for a nebulizer, or as a microfine powder for insufflation, alone or in combination with an inert carrier such as lactose. In such a case, the particles of the formulation will, by way of example and without limitation, have diameters of less than about 50 microns, such as less than about 10 microns.

The agents may be also formulated for local or topical application, such as for application to the skin and mucous membranes (e.g., intranasally), in the form of nasal solutions, gels, creams, and lotions.

Other routes of administration, such as transdermal patches are also contemplated herein. Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957.

In one embodiment, in order to enhance brain delivery of the inhibitor of Nt5e or A1R, the patient is treated in a manner so as to increase the selective permeability of the blood-brain barrier (BBB). Treatments to selectively increase the permeability of the BBB in a patient include, but are not limited to, the administration of about 1 to about 1000 µg/kg body weight, preferably about 10 to about 100 µg/kg bodyweight, of IGF-I (e.g., as a bolus injection to a patient about 0.5 to 10 hours, preferably about 1 hour, before the inhibitor administration).

Inhibitors of Nt5e or A1R or pharmaceutically acceptable derivatives for use in the present invention may be packaged as articles of manufacture containing packaging material and a label that indicates that the inhibitor or pharmaceutically acceptable derivative thereof, is used for modulating the activity Nt5e or A1R for enhancing learning and memory or for treatment of one or more symptoms of at least one relevant disease.

In the methods of the invention, when determination of enhanced learning is involved, it can be measured using methods known in the art, e.g., the DSM-V criteria (American Psychiatric Association, 2013, Diagnostic and Statistical Manual of Mental Disorders (Fifth Edition)).

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Long-Lasting Reopening of the Critical Period of Auditory Cortical Plasticity by Impeding Thalamic Adenosine Materials and Methods Animals.

Young [postnatal day (P) 5-P7] and mature (P45-P56) mice of both sexes were used for all experiments. In experiments with old animals (P210 or older), CBA mice were used. The production and genotyping of the $A_1R^{-/-}$ and $Nt5e^{-/-}$ mutant strains have been previously described[24, 25]. Mutant mouse strains were back-crossed onto the C57BL/6J genetic background for at least 10 generations. The care and use of animals were reviewed and approved by the St. Jude Children's Research Hospital Institutional Animal Care and Use Committee.

Passive Sound Exposure.

Mice were housed in ventilated sound-proof chambers with ad libitum food and water and maintained on a 12:12 hour light:dark cycle. Mice were exposed to continuous sound stimulation for 5 to 14 days, consisting of repeated trains of tones. Each train consisted of 5 tones delivered at 5 Hz. A pure tone of certain frequencies (7 kHz, 7.9 kHz, 9.8 kHz, 11.4 kHz, or 16.4 kHz) was used. The tone duration was 50 ms with 5-ms cosine onset/offset ramps at 70-dB sound pressure level (SPL). Trains were separated by 1 s. Naïve (nonexposed) mice were housed in a similar fashion but received no sound stimulation.

Cortical Map Measurements in the ACx.

Mice were anesthetized with sodium pentobarbital (50 mg/kg) and chlorprothixene (0.2 mg) followed by supplemental doses of sodium pentobarbital (15-25 mg/kg supplements as needed). Spike responses to sound stimulation were recorded from the primary (A1) ACx (depth, 350-420 µm from the pial surface) with Epoxylite-coated tungsten microelectrodes (2.0 MΩ at 1 kHz; FHC, Brunswick, Me.). Frequency response areas (FRAs) were measured with randomly presented tone pips of varying frequency (4.0-44.6 kHz in 0.1-octave increments, 20-ms duration, 5-ms raised cosine onset/offset ramps, 500-ms intertone interval) and level (0- to 70-dB SPL in 10-dB increments). Tones were generated by an electrostatic speaker [Tucker-Davis Technologies (TDT), Alachua, Fla.], which was placed 10 cm from the contralateral ear of the mouse. The ipsilateral ear was plugged with agar. Spike responses to tone pips were amplified with an RA4PA fiber optic preamplifier, filtered (high pass=250 Hz, low pass=5000 Hz), and digitized with an RZ6 real-time processor (TDT). The threshold for spike detection was set at a signal-to-noise ratio of 3:1. TDT System 3 software (OpenEx) controlled both sound stimulus generation and response acquisition and was used for data storage. Cortical maps in the A1 were generated from FRAs measured at 30 to 40 sites per mouse, each separated by 50 to 100 µm. FRAs were analyzed with TDT System 3 software (Open Explorer) for characteristic frequencies (CFs) collated in bins of 0.22 octaves. CF was defined as the tone frequency that elicits spike responses at the lowest sound level. Only short latency (<20 ms) spike responses were used to determine FRAs. Recording sites that were either unresponsive or did not match the tonotopic criteria of A1 were omitted from the data analysis. The location of each recording site was noted on a high-resolution image of A1 collected during data acquisition (Olympus DP72 camera and SZX7 stereo microscope).

Quantitative PCR.

RNA was isolated from the mouse thalamus by using the mirVana RNA isolation kit (Life Technologies, Carlsbad, Calif.). The SuperScript III reverse transcriptase kit (Life Technologies) was used to synthesize cDNA from 500 ng of total RNA. The qPCR was performed using SYBR Green with the following primers: Gapdh: 5'-GTCGGTGT-GAACGGATTTG-3' (SEQ ID NO: 1) and 5'-TAGACTC-CACGACATACTCAGCA-3' (SEQ ID NO: 2), Nt5e: 5'-AACCCCTTTCCTCTCAAATCCA-3' (SEQ ID NO: 3) and 5'-CAGGGCGATGATCTTATTCACAT-3' (SEQ ID NO: 4), Acpp: 5'-AAGGAGTTGAAGTTTGTGACAT-3' (SEQ ID NO: 5) and 5'-TGAGTTGGCCAAATCCTTGT-3' (SEQ ID NO: 6), and Tnap: 5'-ACCTGCCTTAC-CAACTCTT-3' (SEQ ID NO: 7) and 5'-ATTCTTGGCTA-CATTGGTGTT-3' (SEQ ID NO: 8). Expression levels of Nt5e, Acpp, and Tnap were normalized to the housekeeping gene Gapdh for each sample. Samples for each mouse were run in triplicate.

Western Blotting.

Mouse MGv tissues were lysed in ice-cold RIPA buffer [50 mM Tris-HCl (pH 7.4), 1% NP-40, 0.25% sodium deoxycholate, 150 mM NaCl, and 1 mM EDTA] that included protease inhibitor cocktail tablets. A total of 20 µg protein was loaded per lane. Sodium dodecyl sulfate/polyacrylamide gel electrophoresis, protein transfer to polyvinylidene difluoride membranes, and Western blotting were performed using standard methods. The following primary antibodies were used: rabbit anti-Nt5e (1:250, AP2014b; Abgent, San Diego, Calif.) and mouse anti-β-actin (1:10000, A5316; Sigma-Aldrich, St. Louis, Mo.). The secondary antibodies used included anti-rabbit (1:30000, 926-68021; LI-COR Biotechnology, Lincoln, Nebr.) and anti-mouse (1:15000, 926-32212; LI-COR) antibodies conjugated to IR dye 680 or 800. Blots were imaged and quantified using the Odyssey infrared imaging system (LI-COR).

Plasmids, Viral Production, and In Vivo Viral Injections.

Lentivector siRNA plasmids (scramble control 5'-TACGTCCAAGGTCGGGCAGGAAGA-3' (SEQ ID NO: 9), $A_1R$ (123) 5'-CGATGCTACCTTCTGCTTCATCG-TATCCC-3' (SEQ ID NO: 10), $A_1R$ (789) 5'-CCAGAAAC-CCAGCATCCTCATCTACATTG-3' (SEQ ID NO: 11), Nt5e (1264) 5'-ACATTTGACCTCGTCCAAT-TAAAAGGGTC-3' (SEQ ID NO: 12), and Nt5e (1366) 5'-GGAATCCATGTGGTGTACGATATTAACCG-3' (SEQ ID NO: 13)) were generated by Applied Biological Materials, Inc. (Richmond, BC, Canada), and viruses ($1.8 \times 10^8$-$1 \times 10^9$ particles/mL) were produced by the Viral Vector Core at the University of Tennessee Health Science Center (Memphis, Tenn.). Anesthesia was induced in mice by using 2% isoflurane (in 100% $O_2$) and was maintained with 1.5% isoflurane. Craniotomy was performed over the ACx, and a 32-G cannula was inserted into the brain to deliver the virus. Mice were injected with 120-150 nL virus (380-400 nL/h) into the MGv (anterior-posterior, -3.16 mm; lateral ±2.0 mm, ventral, -2.47 mm). The following coordinates were used to inject the virus (540-600 nL/h) into 2 locations in the ACx: anterior-posterior, -2.0 and -2.4 mm; lateral ±3.7 mm, ventral, -0.8 mm. After injections, the incisions were sutured, and the mice were allowed to recover for 2 to 3 h before they were placed in the enriched, tone-exposure chambers for 5 to 14 days.

Measurements of Adenosine Levels.

Mice were deeply anesthetized with Avertin until all deep tendon and corneal reflexes were absent. Then, they were transcardially perfused with ice-cold saline. Following perfusion, brains were rapidly dissected from the calvaria, placed in a cooled mouse brain matrix (Model BS-AL-5000C, Braintree Scientific, Braintree, Mass.), and sliced into 2-mm-thick sections. The brains were then subdissected into the ACx, MGv, and hippocampus. Adenosine was detected and analyzed using HPLC-ECD, as previously described[26]. Adenosine concentrations in tissues were quantified by comparing the peak areas of the sample chromatograms with a standard curve generated from a 4-point concentration curve (12.5, 25, 50 and 100 ng/mL) of external standards (Sigma). Following chromatography, the signal from the electrochemical detector was recorded using a model SS420x integration device (Scientific Software International, Inc., Skokie, Ill.). Additionally, a re-extraction from the pellets generated during the initial extraction was performed to determine if adenosine, ATP, ADP, and AMP were fully extracted. HPLC-ECD analysis of the re-extracted supernatant found no ADO, ATP, ADP, or AMP.

Auditory Learning Task.

The mice were split into two groups: those that have been exposed for 5-7 days to 9.8 kHz pure tone [5 Hz train of tones, the tone duration was 50 ms with 5 ms cosine onset/offset ramps at 70 dB sound pressure level (SPL)] prior to training and those that have been housed for 5-7 days in silence prior to training. Both groups were housed in the sound-proof chambers. During this period, the animals began the food restriction regiment (see below). Once the training began the mice were no longer housed in the sound-proof chambers. Mice were food restricted at 70-85% of their daily intake, such that they maintain ~20% body mass reduction. This was done to motivate lever pressing for food, which increases the likelihood of learning the operant task[27]. Body mass were recorded every three days, food ration was adjusted as required to maintain the 20% body mass reduction. Water was available ad libitum. A standard pelleted chow was used (20 mg dustless precision pellets, Bio-Serv, Frenchtown, N.J.), unless otherwise stated. Food intake during training, described below, was measured and food was made available after each session to assure each animal is adequately fed.

Training.

Animals training to associate a sound with pressing a lever were performed similarly to previously described protocols[7,28-30]. Phase 1: Lever Pressing Task Learning. On each day of Phase 1, mice were placed into an operant conditioning chamber (MED-307A, MedAssociates, Georgia, Vt.) for one hour. At the beginning of the session, one lever was made available and the house light turned on. During this hour each lever press earned one food pellet (fixed ratio (FR) 1). If 50 reinforcements were obtained the session was terminated, with the retraction of the lever and house light turning off. If the 50 reinforcements were not obtained the lever retracted and house light turned off at the end of the 1-hour. The animal was removed from the chamber when the session was over. Phase 1 session continued daily until the mice reached 50 reinforcements, typically 2-3 days; at this point the animals began Phase 2 of training. If an individual did not reach 50 reinforcements after 4 sessions of Phase 1, they were removed from the study. Phase 2: Cued Responding. Each animal was placed into the operant chamber and given a Go/NoGo-task. In brief, the session began with the presentation of the lever and the turning on of the house light. A conditioned stimulus

[CS, 70 db SPL, white noise] was played for 5 seconds, during this time a lever press was rewarded with a single food pellet. Following the lever press, the CS tone stopped and an intertrial interval of 10-20 s began before the next CS was presented. If the lever was pressed during the intertrial interval, a time-out occurred (house light turned off for 10-20 s before the start of the next trial). The daily Phase 2 sessions were given a time limit of 1 hour or 50 reinforcements. Phase 3 commenced once the animal successfully learnt to respond to the auditory cue (~70% of lever presses during tone). Phase 3a: Tone Discrimination. When the session began the lever was presented and house light turned on. The CS+ for this session was a pure tone (9.8 kHz, 70 db SPL, 5 Hz train of pulses as in the tone exposure experiments, train duration 5 sec), with the presentation/reward schedule of the CS+ the same as in Phase 2. Additional pure tones were played as CS− (non-rewarded, foil tones; 6.8 kHz or 14.2 kHz) in a similar fashion as CS+. Lever presses during the CS− resulted in a time out, the same as in Phase 2, and counted as 'false-alarm' responses. The session ended after 1 hour or when the animal earned 50 food pellets. Comparisons was made between groups based upon the percentage of correct responses to CS+vs. 'false-alarm' responses to CS−. Phase 3b: Control for generalized tone learning. These experiments were performed in a different group of animals that were also exposed to 9.8 kHz or silence for 5-7 days in the sound-proof chambers. These animals were trained through Phases 1 and 2 and not trained in Phases 3a. The CS+ for these experiments was one of the CS− tones from Phase 3a (6.8 kHz or 14.2 kHz) with the CS− 9.8 kHz and the remaining CS− tone from Phase 3a. Testing auditory memory: Animals that completed Phase 3a and 3b continued to be food restricted and housed without pure tone exposure. To assess the long-term effects of the tone exposure and subsequent operant task/tone discrimination learning, the animals were run through their Phase 3 task again after one week. The specific CS+/CS− used was maintained for each individual, as were all other aspects of the session.

Statistical Analyses.

Data are presented as means±SEM. All statistics were computed using SigmaPlot and SigmaStat software (Systat Software, Inc., Point Richmond, Calif.). In vivo FRA data are presented as the percentage of A1 sites responding to best frequencies collected in 0.22-octave bins. Percentage data were arcsine transformed, and means were analyzed by two-way ANOVA (factored by frequency and training protocol (sound exposure vs. no sound exposure). If the ANOVA result was significant, then a Tukey post-hoc multiple-comparison procedure was used to make pairwise comparisons of FRA means. Differences in mean data were considered significant if the P-value of the test result was less than 0.05.

Results

To test if cortical map plasticity can be extended beyond the early critical period by restricting adenosine signaling through $A_1R$, a comparison between the plasticity of cortical maps in mature (P45-P56) wild-type (WT) and $A_1R^{-/-}$ mice reared in an environment enriched with a pure tone for 5 to 14 days was made (FIG. 1a). The cortical organization was examined by recording tone-evoked neuronal responses during 30 to 40 microelectrode penetrations at the cortical depth corresponding to the thalamorecipient layer (L) ¾ of the mouse ACx. At each site, neuronal responses to a wide range of tone frequencies and intensities were recorded. The frequency-intensity responses provided an objective basis for defining the characteristic frequency (CF), which is the tone frequency at which responses could be evoked at the lowest stimulus intensity, for each site[6]. As in previous studies[6,31-33], the primary ACx (A1) was organized tonotopically in unexposed (naïve) mice, with isofrequency bands oriented approximately orthogonally to a rostrocaudal axis (FIG. 1b). Also consistent with previous studies, the cortical maps in mature WT mice did not expand or shrink after passive tone exposure (FIG. 1b). Specifically, no differences were found between the cortical maps of mature WT mice, whether they were naïve or exposed to the 7-kHz tone. However, the percentage of recording sites with a CF that was comparable to the exposure frequency was substantially larger in sound-exposed $A_1R^{-/-}$ mice (FIG. 1c). This increase was tone frequency-specific. Thus, $A_1R^{-/-}$ mice exposed to 7.9 or 16.4 kHz showed a substantial increase in the percentage of respective recording sites compared to that in naïve $A_1R^{-/-}$ mice. Furthermore, naïve $A_1R^{-/-}$ mice did not show a significant change in cortical representations compared to that of naïve WT mice.

Figure 1G:
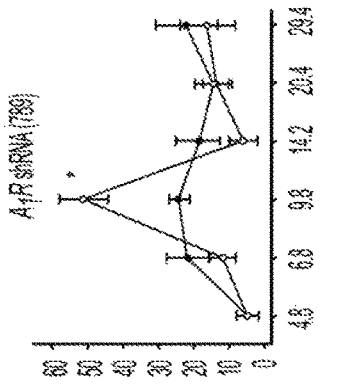
Figure 1F:
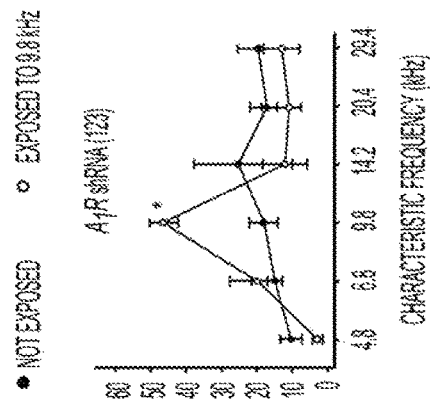
Figure 1E:
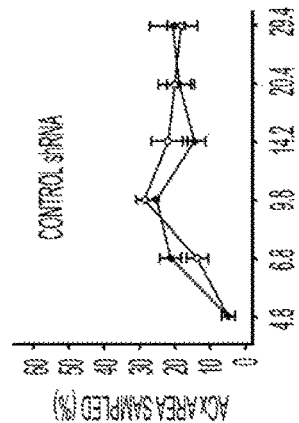
Figure 1D:
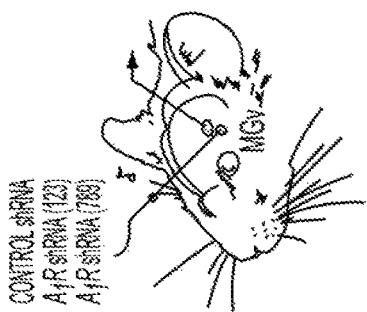
Figure 1J:
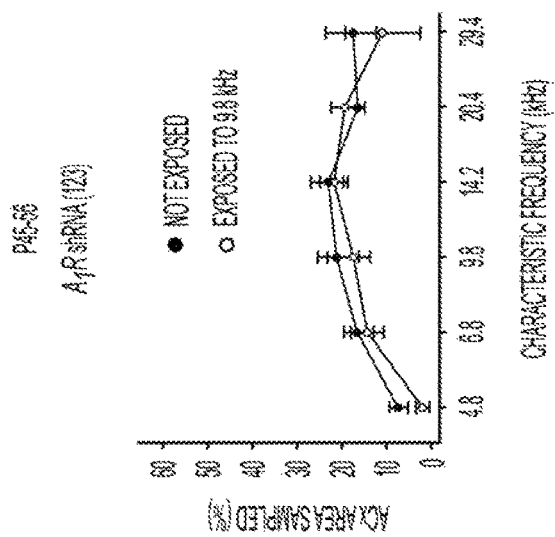
Figure 1I:
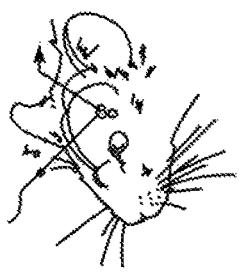
Figure 1H:
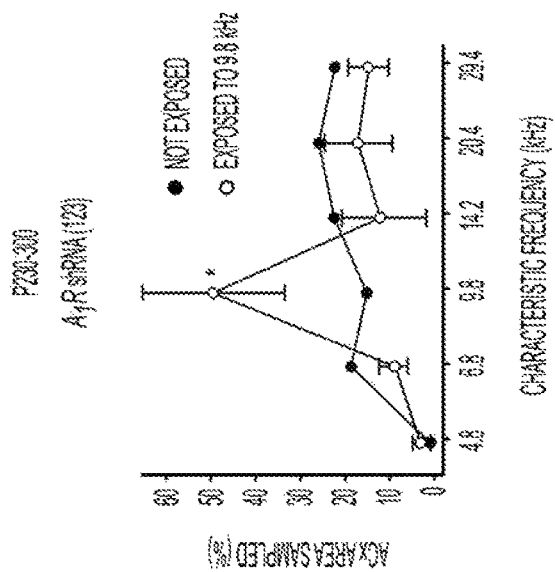

The shRNA approach was utilized to determine which brain region underlies this cortical map plasticity in adult mice (FIG. 1d). Knocking down $A_1R$ only in the auditory thalamus (the ventral part of the medial *geniculate* nuclei [MGv]) with 2 different shRNAs against $A_1R$ mRNA [$A_1R$ shRNA (123) and $A_1R$ shRNA (789)] [$A_1R$ (123) 5'-CGAT-GCTACCTTCTGCTTCATCGTATCCC-3' (SEQ ID NO: 10), $A_1R$ (789) 5'-CCAGAAACCCAGCATCCTCATCTA-CATTG-3' (SEQ ID NO: 11)] was sufficient to induce ACx map plasticity in adult mice by passive exposure to a 9.8-kHz tone. Naïve mice and those treated with a scrambled (control) shRNA (5'-TACGTCCAAGGTCGGGCAG-GAAGA-3' (SEQ ID NO: 9; coding DNA sequence)) showed no cortical map plasticity (FIG. 1e). Remarkably, such cortical map plasticity could be induced long beyond the early critical period. In very mature (7- to 8-month-old) mice with knocked-down $A_1R$ in the auditory thalamus, exposure to 9.8-kHz tone produced a substantial increase in the percentage of sites with a CF of 9.8 kHz compared to that in naïve age-matched mice (FIGS. 1f-1g). In contrast, knocking down $A_1R$ with the same $A_1R$ shRNAs in the ACx, with or without sound exposure, did not induce cortical map plasticity (FIG. 1j).

Figures 2A, 2B:
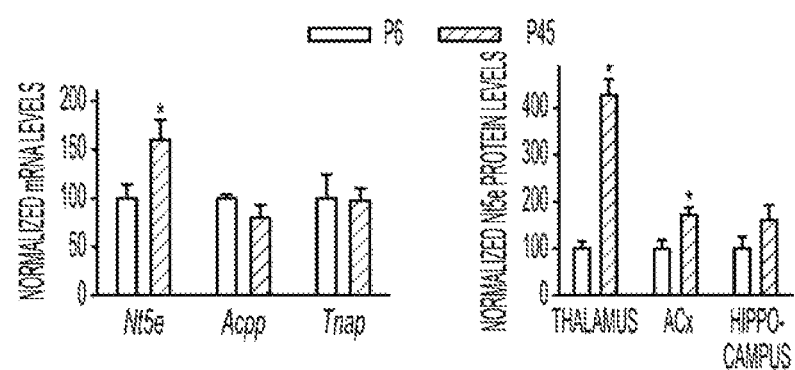
Figures 2C, 2D:
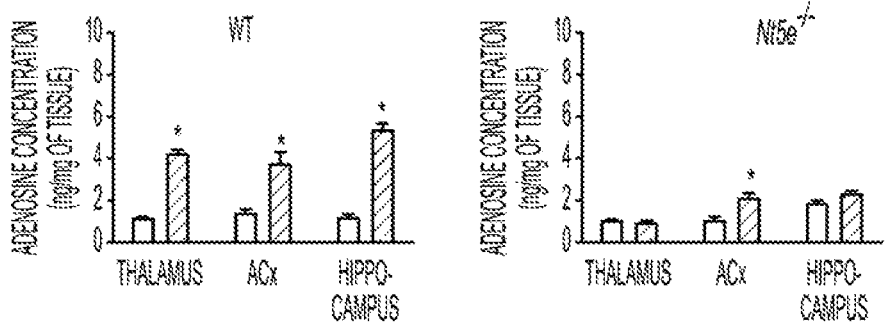

The extension of the critical period for cortical map plasticity in response to passive sound exposure during adulthood by eliminating thalamic adenosine signaling suggests that the adenosine machinery (or its components) is developmentally regulated in the auditory thalamus and thus underlies the duration of the early critical period. Among ectonucleotidases that hydrolyze AMP to adenosine in the mammalian central nervous system[34], only Nt5e mRNA is significantly elevated in the thalamus of mature mice compared to that in neonates, though levels of Acpp and Tnap mRNAs did not change with age (FIG. 2a). The level of Nt5e protein was substantially higher in the thalamus of mature mice than in neonatal mice, whereas in the ACx and hippocampus, Nt5e was slightly elevated or the same between mature and neonatal mice (FIG. 2b). Consistent with Nt5e upregulation in the mature brain, the total adenosine level was dramatically higher in the thalamus, ACx, and hippocampus of mature mice than in neonates (FIG. 2c). This age-dependent elevation was either eliminated in the thalamus and hippocampus or substantially reduced in the ACx of $Nt5e^{-/-}$ mice (FIG. 2d). This result suggests that the age-dependent Nt5e-mediated elevation in adenosine production regulates the early critical period of cortical map plasticity.

Consistent with this hypothesis, mature Nt5e$^{-/-}$ mice, but not WT littermates, reared in an environment enriched with 11.4-kHz tonal stimulation showed a substantially greater percentage of sites with a CF of 11.4 kHz compared to that in naïve mice (FIGS. 2e,2f). Similarly, mature WT mice injected with 2 different Nt5e shRNAs (Nt5e shRNA (1264) and Nt5e shRNA (1366)) [Nt5e (1264) 5'-ACATTTGAC-CTCGTCCAATTAAAAGGGTC-3' (SEQ ID NO: 12), and Nt5e (1366) 5'-GGAATCCATGTGGTGTACGATAT-TAACCG-3' (SEQ ID NO: 13)] into the auditory thalamus and exposed to 11.4 kHz had a significantly larger percentage of sites with a CF of 11.4 kHz compared to that in naïve mice (FIGS. 2g,2h).

These data demonstrate that an Nt5e-mediated, age-dependent increase in adenosine production in the auditory thalamus terminates the early critical period of cortical map plasticity in the ACx. In adults, elevated adenosine levels, as a negative regulator of glutamate release, restricts TC LTP and LTD at TC projections and thus prevents cortical map plasticity via passive sound exposure. Impairing thalamic adenosine machinery by impairing Nt5e-dependent adenosine production or $A_1R$-mediated adenosine signaling is sufficient to unmask cortical map plasticity in adults aged far beyond the early critical period. It follows that preventing adenosine production or signaling in the auditory thalamus can rejuvenate auditory learning capabilities in adults.

Example 2: Non-Auditory Sensory Learning

Visual Learning.

The visual learning task is performed as described previously[35-37]. Visual discrimination task training involves a forced-choice swim test in a Y-maze. Water temperature is kept constant (21±2° C.). Trials begin when the mouse enters the chamber that allows for both visual cues to be seen. Both ends of the Y-maze have a monitor that displays visual cues that serve as the reinforced or non-reinforced stimulus, the side displaying the reinforced cue has a submerged platform. Once reached, the mouse remains on the platform for 30 s before being removed from the water. This completes the training unit. The non-reinforced stimulus side does not contain a platform and choosing that side results in the mouse being restarted immediately in the training task, until the reinforced side is chosen or five incorrect trials. Each training day consists of 3 sessions of 10 training units. After the unit is completed, the mice are placed into a warming chamber until the start of the next training unit 1-2 minutes later, with 10-20 minutes between training sessions. The location of the reinforced stimulus/platform is pseudo-randomized. A training unit is scored as a 'successful' only when the platform is reached on the first trial of the unit. Comparisons are made among treatment groups for the rate of learning, as determined by the number of 'successful' training units over the course of the training regimen. The visual cue used to indicate the correct side is maintained throughout the experiment for each individual while the incorrect side cue is variable, to avoid learning of a negative cue that could skew the learning curve. The reinforced visual stimulus is not be the same for all animals, to minimize the chance of an innate visual bias.

Somatosensoty (Tactile) Learning.

Mice are trained to perform object location discrimination through operant conditioning[38,39]. The stimulus is a pole (0.9 mm in diameter), presented at one of two possible positions. The two pole positions are 4.29 mm apart along the anterior-posterior axis (40 deg of whisking angle) and are constant across sessions. The posterior pole position is 5 mm from the whisker pad. A two-spout lickport (4.5 mm apart) is used to deliver water rewards and record licks. Mouth movements (reaction time) are monitored using a photodiode and an infrared laser diode (Thorlabs). High speed video is taken at 1 kHz using Mikrotron Eosens Camera (Norpix, MC1362) to track the C2 whisker. At the beginning of each trial, the vertical pole is moved into the plane within reach of the C2 whisker (0.2 s travel time). The sound produced by mechanically moving the pole triggers whisking before the pole is within reach. The pole remains within reach for 1 second, after which it is retracted. The retraction time is 0.2 second, of which the pole remains within reach in the first 0.1 second. The delay epoch lasts for another 1-2 seconds after the completion of pole retraction. An auditory "response" cue indicates the end of the delay epoch (pure tone, 3.4 kHz, 0.1 s duration). Licking early during the trial is punished by a loud "alarm" sound (siren buzzer, 0.05 s duration, RadioShack, 273-079), followed by a brief timeout (1-2 s). Continued licking triggers additional timeouts. These trials are excluded from the analyses. Licking the incorrect lickport triggers a timeout (2-5 s). Sessions are terminated when signs of fatigue are observed (e.g. reduced whisking, occurrence of "no lick" trials). The total training time to criterion performance (>70% correct) is 3-4 weeks.

REFERENCES

1. Reed, A., et al. "Cortical map plasticity improves learning but is not necessary for improved performance," *Neuron* 70, 121 (2011).
2. Schreiner, C. E. and Polley, D. B. "Auditory map plasticity: diversity in causes and consequences," *Curr Opin Neurobiol* 24, 143 (2014).
3. Recanzone, G. H., Schreiner, C. E., and Merzenich, M. M. "Plasticity in the frequency representation of primary auditory cortex following discrimination training in adult owl monkeys," *J Neurosci* 13, 87 (1993).
4. Barkat, T. R., Polley, D. B., and Hensch, T. K. "A critical period for auditory thalamocortical connectivity," *Nat Neurosci* 14, 1189 (2011).
5. de Villers-Sidani, E., Chang, E. F., Bao, S., and Merzenich, M. M. "Critical period window for spectral tuning defined in the primary auditory cortex (A1) in the rat," *J Neurosci* 27, 180 (2007).
6. Zhang, L. I., Bao, S., and Merzenich, M. M. "Persistent and specific influences of early acoustic environments on primary auditory cortex," *Nat Neurosci* 4, 1123 (2001).
7. Han, Y. K., Kover, H., Insanally, M. N., Semerdjian, J. H., and Bao, S. "Early experience impairs perceptual discrimination," *Nat Neurosci* 10, 1191 (2007).
8. Bakin, J. S. and Weinberger, N. M. "Induction of a physiological memory in the cerebral cortex by stimulation of the nucleus basalis," *Proc Natl Acad Sci USA* 93, 11219 (1996).
9. Bao, S., Chan, V. T., and Merzenich, M. M. "Cortical remodelling induced by activity of ventral tegmental dopamine neurons," *Nature* 412, 79 (2001).
10. Blundon, J. A. and Zakharenko, S. S. "Presynaptic gating of postsynaptic synaptic plasticity: a plasticity filter in the adult auditory cortex," *Neuroscientist* 19, 465 (2013).
11. Feldman, D. E. and Brecht, M. "Map plasticity in somatosensory cortex," *Science* 310, 810 (2005).

12. Hubener, M. and Bonhoeffer, T. "Neuronal Plasticity: Beyond the Critical Period," *Cell* 159, 727 (2014).
13. Oberlaender, M., Ramirez, A., and Bruno, R. M. "Sensory experience restructures thalamocortical axons during adulthood," *Neuron* 74, 648 (2012).
14. Takesian, A. E. and Hensch, T. K. "Balancing plasticity/stability across brain development," *Prog Brain Res* 207, 3 (2013).
15. Blundon, J. A., Bayazitov, I. T., and Zakharenko, S. S. "Presynaptic gating of postsynaptically expressed plasticity at mature thalamocortical synapses," *J Neurosci* 31, 16012 (2011).
16. Chun, S., Bayazitov, I. T., Blundon, J. A., and Zakharenko, S. S. "Thalamocortical long-term potentiation becomes gated after the early critical period in the auditory cortex," *J Neurosci* 33, 7345 (2013).
17. Crair, M. C. and Malenka, R. C. "A critical period for long-term potentiation at thalamocortical synapses," *Nature* 375, 325 (1995).
18. Froemke, R. C., Merzenich, M. M., and Schreiner, C. E. "A synaptic memory trace for cortical receptive field plasticity," *Nature* 450, 425 (2007).
19. Kilgard, M. P. and Merzenich, M. M. "Cortical map reorganization enabled by nucleus basalis activity," *Science* 279, 1714 (1998).
20. Manzoni, O. J., Manabe, T., and Nicoll, R. A. "Release of adenosine by activation of NMDA receptors in the hippocampus," *Science* 265, 2098 (1994).
21. Mitchell, J. B., Lupica, C. R., and Dunwiddie, T. V. "Activity-dependent release of endogenous adenosine modulates synaptic responses in the rat hippocampus," *J Neurosci* 13, 3439 (1993).
22. Yawo, H. and Chuhma, N. "Preferential inhibition of omega-conotoxin-sensitive presynaptic Ca2+ channels by adenosine autoreceptors," *Nature* 365, 256 (1993).
23. Dunwiddie, T. V. and Masino, S. A. "The role and regulation of adenosine in the central nervous system," *Annu Rev Neurosci* 24, 31 (2001).
24. Johansson, B., et al. "Hyperalgesia, anxiety, and decreased hypoxic neuroprotection in mice lacking the adenosine A1 receptor," *Proc Natl Acad Sci USA* 98, 9407 (2001).
25. Thompson, L. F., et al. "Crucial role for ecto-5'-nucleotidase (CD73) in vascular leakage during hypoxia," *J Exp Med* 200, 1395 (2004).
26. Pani, A. K., Jiao, Y., Sample, K. J., and Smeyne, R. J. "Neurochemical measurement of adenosine in discrete brain regions of five strains of inbred mice," *PLoS One* 9, e92422 (2014).
27. Rowland, N. E., Vaughan, C. H., Mathes, C. M., and Mitra, A. "Feeding behavior, obesity, and neuroeconomics," *Physiol Behav* 93, 97 (2008).
28. Froemke, R. C., et al. "Long-term modification of cortical synapses improves sensory perception," *Nat Neurosci* 16, 79 (2013).
29. Reed, A., et al. "Cortical map plasticity improves learning but is not necessary for improved performance," 70, 121 (2011).
30. Ward, R. D., Simpson, E. H., Kandel, E. R., and Balsam, P. D. "Modeling motivational deficits in mouse models of schizophrenia: behavior analysis as a guide for neuroscience," *Behav Processes* 87, 149 (2011).
31. Insanally, M. N., Kover, H., Kim, H., and Bao, S. "Feature-dependent sensitive periods in the development of complex sound representation," *J Neurosci* 29, 5456 (2009).
32. Polley, D. B., Read, H. L., Storace, D. A., and Merzenich, M. M. "Multiparametric auditory receptive field organization across five cortical fields in the albino rat," *J Neurophysiol* 97, 3621 (2007).
33. Hackett, T. A., Barkat, T. R., O'Brien, B. M., Hensch, T. K., and Polley, D. B. "Linking topography to tonotopy in the mouse auditory thalamocortical circuit," *J Neurosci* 31, 2983 (2011).
34. Street, S. E., et al. "Tissue-nonspecific alkaline phosphatase acts redundantly with PAP and NT5E to generate adenosine in the dorsal spinal cord," *J Neurosci* 33, 11314 (2013).
35. Prusky, G. T., West, P. W., and Douglas, R. M. "Behavioral assessment of visual acuity in mice and rats," *Vision Res* 40, 2201 (2000).
36. Trevino, M., Frey, S., and Kohr, G. "Alpha-1 adrenergic receptors gate rapid orientation-specific reduction in visual discrimination," *Cereb Cortex* 22, 2529 (2012).
37. Trevino, M. "Stimulus similarity determines the prevalence of behavioral laterality in a visual discrimination task for mice," *Sci Rep* 4, 7569 (2014).
38. Guo, Z. V., et al. "Flow of cortical activity underlying a tactile decision in mice," *Neuron* 81, 179 (2014).
39. O'Connor, D. H., et al. "Vibrissa-based object localization in head-fixed mice," *J Neurosci* 30, 1947 (2010).

LIST OF SEQUENCES

| SEQ ID NO | Sequence | Description |
|---|---|---|
| 1 | GTCGGTGTGAACGGATTTG | Gapdh primer |
| 2 | TAGACTCCACGACATACTCAGCA | Gapdh primer |
| 3 | AACCCCTTTCCTCTCAAATCCA | Nt5e primer |
| 4 | CAGGGCGATGATCTTATTCACAT | Nt5e primer |
| 5 | AAGGAGTTGAAGTTTGTGACAT | Acpp primer |
| 6 | TGAGTTGGCCAAATCCTTGT | Acpp primer |
| 7 | ACCTGCCTTACCAACTCTT | Tnap primer |
| 8 | ATTCTTGGCTACATTGGTGTT | Tnap primer |
| 9 | TACGTCCAAGGTCGGGCAGGAAGA | DNA encoding shRNA scramble control |

| SEQ ID NO | Sequence | Description |
|---|---|---|
| 10 | CGATGCTACCTTCTGCTTCATCGTATCCC | DNA encoding shRNA A1R (123) |
| 11 | CCAGAAACCCAGCATCCTCATCTACATTG | DNA encoding shRNA A1R (789) |
| 12 | ACATTTGACCTCGTCCAATTAAAAGGGTC | DNA encoding shRNA Nt5e (1264) |
| 13 | GGAATCCATGTGGTGTACGATATTAACCG | DNA encoding shRNA Nt5e (1366) |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

What is claimed is:

1. A method for improving learning and/or memory in a subject in need thereof comprising administering to said subject an inhibitor of expression or function of (i) ecto-5'-nucleotidase (Nt5e) or (ii) A1 adenosine receptor (A1R), wherein said inhibitor is administered in an amount which is effective for inhibiting expression or function of Nt5e or A1R in the brain of the subject, wherein the learning and memory are selected from auditory, visual, and somatosensory.

2. The method of claim 1, wherein said learning and/or memory is learning and/or memory of an acoustic information.

3. The method of claim 2, wherein the subject is simultaneously exposed to (i) the inhibitor and (ii) to a sound.

4. The method of claim 3, wherein the sound is in the range 20 Hz-20 kHz.

5. The method of claim 3, comprising first administering the inhibitor to the subject and then exposing the subject to the sound at around the time when the inhibitor reaches the effective concentration in the brain.

6. The method of claim 1, wherein the subject is an adult or a child of an age beyond the early critical period for said learning.

7. A method for treating a learning disorder or a neurological disease associated with an abnormal auditory, visual, or somatosensory perception in a subject in need thereof comprising administering to said subject an inhibitor of expression or function of (i) ecto-5'-nucleotidase (Nt5e) or (ii) A1 adenosine receptor (A1R), wherein said inhibitor is administered in an amount which is effective for inhibiting expression or function of Nt5e or A1R in the brain of the subject.

8. The method of claim 7, wherein the learning disorder or the neurological disease is associated with an abnormal auditory perception in the subject.

9. The method of claim 8, wherein the neurological disease is selected from tinnitus, Williams-Beuren syndrome, and schizophrenia.

10. The method of claim 1, wherein the inhibitor is selected from interfering RNA molecules, dsRNA, RNA polymerase III transcribed DNAs, ribozymes, and antisense nucleic acids.

11. The method of claim 1, wherein the inhibitor is a compound having a structure according to Formula I:

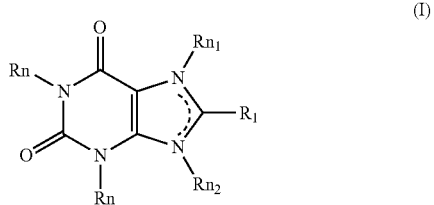

wherein $R_1$ is selected from hydrogen, —F; —Cl; —Br; —I; —OH, —OR*; —$NH_2$; —NHR*; —N(R*)$_2$; —N(R*)$_3^+$; —SH; —SR*; —CN; —NC; —(C=O)—R*; —CHO; —$CO_2$H; —$CO_2$; —$CO_2$R*; —(C=O)—

—S—R*; —O—(C=O)—H; —O—(C=O)—R*; —S—(C=O)—R*; —(C=O)—NH$_2$; —(C=O)—N(R*)$_2$; —SCN; —NCS; —NSO; —SO$_2$—R*; —O—S(=O)$_2$—R*; —S(=O)$_2$—OR*; —N$_2$—R*; —N(C$_2$H$_4$); —Si(R*)$_3$; —CF$_3$; —O—CF$_3$; —PR*$_2$; —O—P(=O)(OR*)$_2$; —P(=O)(OR*)$_2$; perfluoroalkyl; an aliphatic C$_1$-C$_{20}$ hydrocarbon radical; a C$_1$-C$_{12}$ aromatic hydrocarbon radical; and a C$_1$-C$_{12}$ heteroaryl radical;

where R* is independently at each occurrence hydrogen or a straight chained, branched, or cyclic C$_1$-C$_{20}$ hydrocarbon radical, which is saturated, partially saturated, or aromatic, each of which is optionally substituted with 1-6 heteroatoms selected from nitrogen, oxygen, sulfur, phosphorus, and halogen;

R$_n$ is independently at each occurrence hydrogen or a straight chained, branched, or cyclic saturated, partially saturated, or aromatic C$_1$-C$_{20}$ hydrocarbon radical, optionally substituted with 1-12 heteroatoms selected from nitrogen, oxygen, sulfur, phosphorus, and halogen;

Rn$_1$ is Rn or, if Rn$_2$ is present, Rn$_1$ is absent; and
Rn$_2$ is Rn or, if Rn$_1$ is present, Rn$_2$ is absent;

and pharmaceutically acceptable salts thereof.

12. The method of claim 11, wherein the inhibitor is a compound having a structure according to Formula Ia:

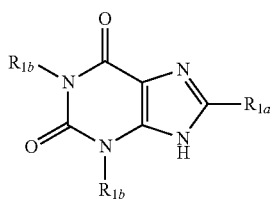

(Ia)

wherein R$_{1a}$ is selected from hydrogen, an aliphatic C$_1$-C$_{20}$ hydrocarbon radical; a C$_1$-C$_{12}$ aromatic hydrocarbon radical; a C$_1$-C$_{12}$ heteroaryl radical, and a combination thereof; and R$_{1b}$ is independently at each occurrence selected from hydrogen; a straight chained, branched, or cyclic saturated, partially saturated, and an aromatic C$_1$-C$_{16}$ hydrocarbon radical;

where R* is independently at each occurrence hydrogen or a straight chained, branched, or cyclic C$_1$-C$_{20}$ hydrocarbon radical, which is saturated, partially saturated, or aromatic, each of which is optionally substituted with 1-6 heteroatoms selected from nitrogen, oxygen, sulfur, phosphorus, and halogen, and pharmaceutically acceptable salts thereof.

13. The method of claim 11, wherein the inhibitor is a compound having a structure according to Formula Ib:

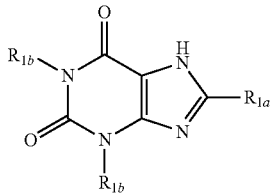

(Ib)

wherein R$_{1a}$ is selected from hydrogen, an aliphatic C$_1$-C$_{20}$ hydrocarbon radical; a C$_1$-C$_{12}$ aromatic hydrocarbon radical; a C$_1$-C$_{12}$ heteroaryl radical, and a combination thereof; and R$_{1b}$ is independently at each occurrence selected from hydrogen; and a straight chained, branched, or cyclic saturated, partially saturated, or aromatic C$_1$-C$_{16}$ hydrocarbon radical;

where R* is independently at each occurrence hydrogen or a straight chained, branched, or cyclic C$_1$-C$_{20}$ hydrocarbon radical, which is saturated, partially saturated, or aromatic, each of which is optionally substituted with 1-6 heteroatoms selected from nitrogen, oxygen, sulfur, phosphorus, and halogen, and pharmaceutically acceptable salts thereof.

14. The method of claim 11, wherein the inhibitor is a compound having a structure selected from Formulas Ic-Ir:

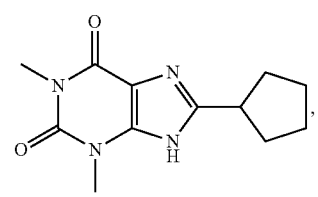

(Ic)

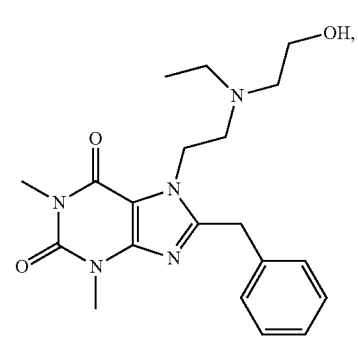

(Id)

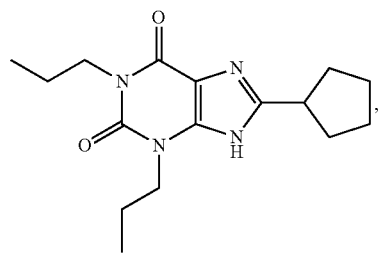

(Ie)

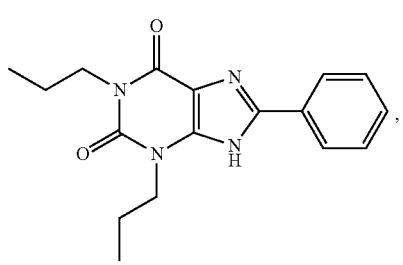

(If)

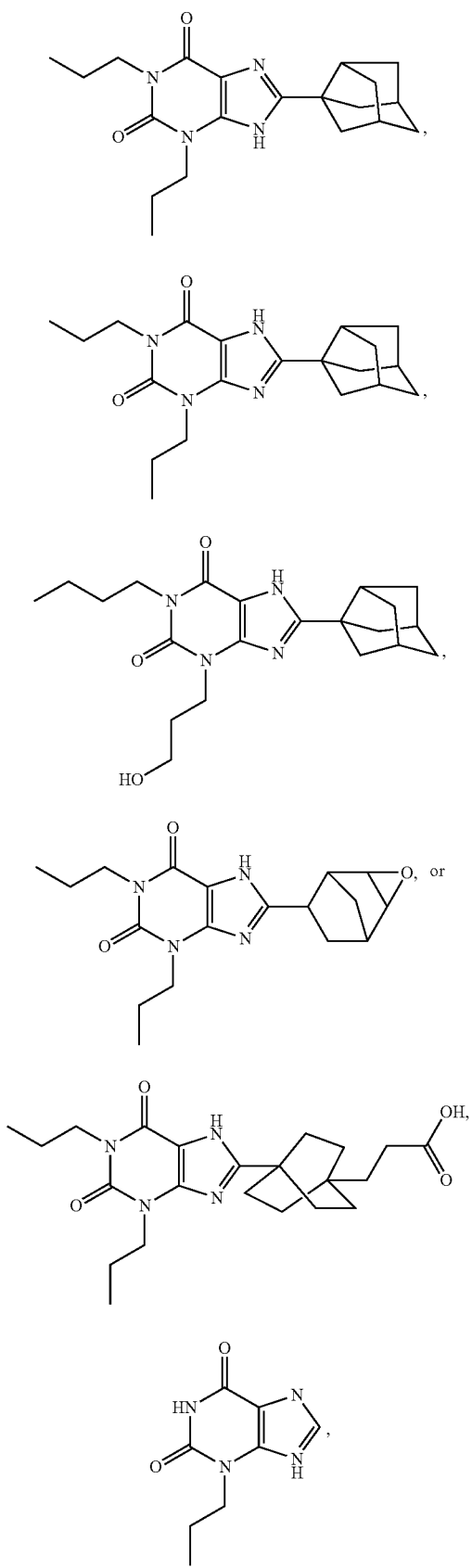
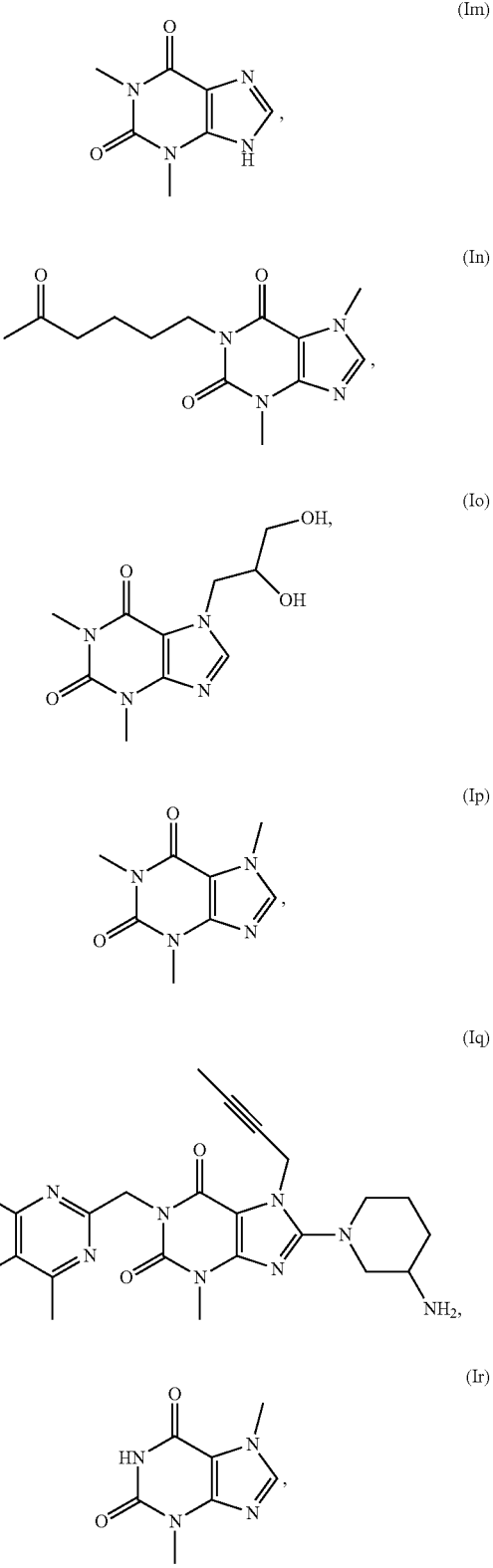
and pharmaceutically acceptable salts thereof.
15. The method of claim 1, wherein the inhibitor is a compound having a structure according to Formula II:

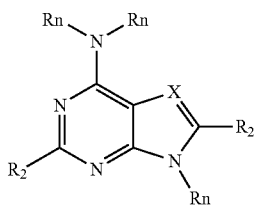

(II)

wherein X is CH or N;

R$_2$ is independently at each occurrence selected from hydrogen, —F; —Cl; —Br; —I; —OH, —OR*; —NH$_2$; —NHR*; —N(R*)$_2$; —N(R*)$_3^+$; —SH; —SR*; —CN; —NC; —(C=O)—R*; —CHO; —CO$_2$H; —CO$_2$; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —SCN; —NCS; —NSO; —SO$_2$—R*; —O—S(=O)$_2$—R*; —S(=O)$_2$—OR*; —N$_2$—R*; —N(C$_2$H$_4$); —Si(R*)$_3$; —CF$_3$; —O—CF$_3$; —PR*$_2$; —O—P(=O)(OR*)$_2$; —P(=O)(OR*)$_2$; perfluoroalkyl; an aliphatic C$_1$-C$_{20}$ hydrocarbon radical; a C$_1$-C$_{12}$ aromatic hydrocarbon radical; and a C$_1$-C$_{12}$ heteroaryl radical; where R* is independently at each occurrence hydrogen or a straight chained, branched, or cyclic C$_1$-C$_{20}$ hydrocarbon radical, which is saturated, partially saturated, or aromatic, each of which is optionally substituted with 1-6 heteroatoms selected from nitrogen, oxygen, sulfur, phosphorus, and halogen;

Rn is independently at each occurrence selected from hydrogen or a straight chained, branched, or cyclic saturated, partially saturated, or aromatic C$_1$-C$_{20}$ hydrocarbon radical, and a C$_1$-C$_{20}$ carbohydrate, optionally substituted with 1-12 heteroatoms selected from nitrogen, oxygen, sulfur, phosphorus, and halogen; and pharmaceutically acceptable salts thereof.

16. The method of claim 15, wherein the inhibitor is a compound having a structure of Formula IIa or Formula IIb:

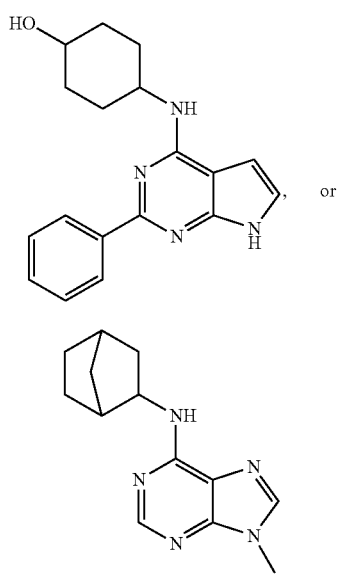

and pharmaceutically acceptable salts thereof.

17. The method of claim 15, wherein the inhibitor is a compound having a structure according to any one of Formulas IIc-IIe:

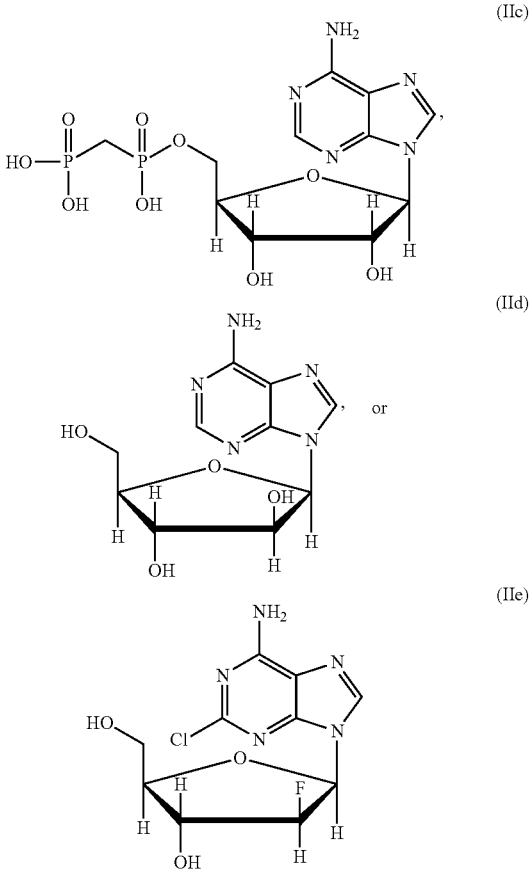

and pharmaceutically acceptable salts thereof.

18. The method of claim 1, wherein the inhibitor is a compound having a structure according to Formula III:

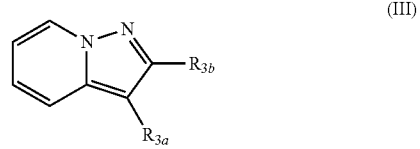

(III)

wherein R$_{3a}$ and R$_{3b}$ are independently selected from hydrogen, —F; —Cl; —Br; —I; —OH, —OR*; —NH$_2$; —NHR*; —N(R*)$_2$; —N(R*)$_3^-$; —SH; —SR*; —CN; —NC; —(C=O)—R*; —CHO; —CO$_2$H; —CO$_2$; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —SCN; NCS; —NSO; —SO$_2$—R*; —O—S(=O)$_2$—R*; —S(=O)$_2$—OR*; —N$_2$—R*; —N(C$_2$H$_4$); —Si(R*)$_3$; —CF$_3$; —O—CF$_3$; —PR*$_2$; —O—P(=O)(OR*)$_2$; —P(=O)(OR*)$_2$; perfluoroalkyl; an aliphatic C$_1$-C$_{20}$ hydrocarbon radical; a C$_1$-C$_{12}$ aromatic hydrocarbon radical; a C$_1$-C$_{12}$ heteroaryl radical; and combinations thereof; where R* is independently at each occurrence hydrogen or a straight chained, branched, or cyclic C$_1$-C$_{20}$ hydrocarbon radical, which is saturated, partially saturated, or aromatic, each of which is optionally substituted with 1-6 heteroatoms selected from nitrogen, oxygen, sulfur, phosphorus, and halogen;

and pharmaceutically acceptable salts thereof.

19. The method of claim 18, wherein the inhibitor is a compound having a structure according to Formula IIIa:

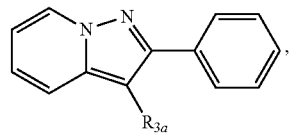

(IIIa)

wherein $R_{3a}$ is hydrogen, acyl, or a $C_1$-$C_{20}$ hydrocarbon radical, which is saturated, partially saturated, or aromatic, each of which is optionally substituted with 1-6 heteroatoms selected from nitrogen, oxygen, sulfur, phosphorus, and halogen.

20. The method of claim 18, wherein the inhibitor is a compound having a structure selected from Formulas IIIb-IIIh:

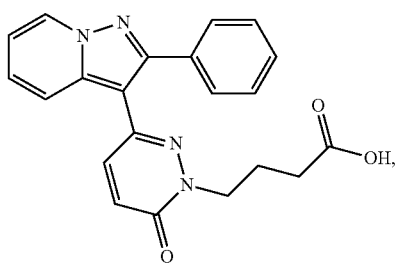

(IIIb)

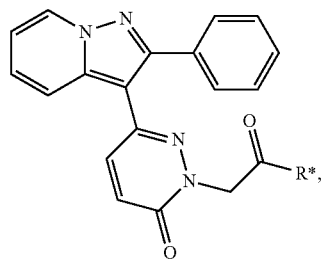

(IIIc)

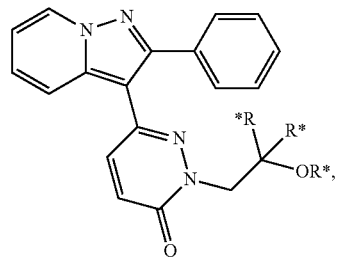

(IIId)

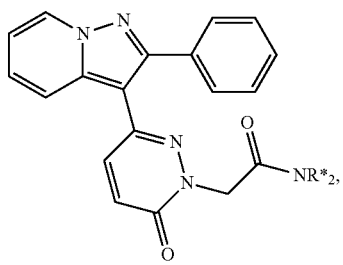

(IIIe)

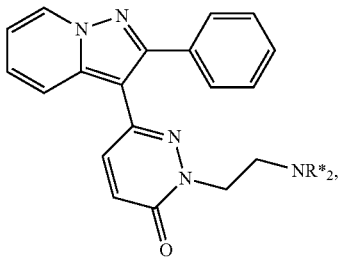

(IIIf)

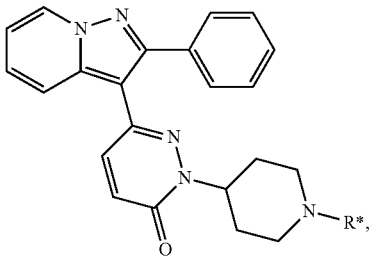

(IIIg)

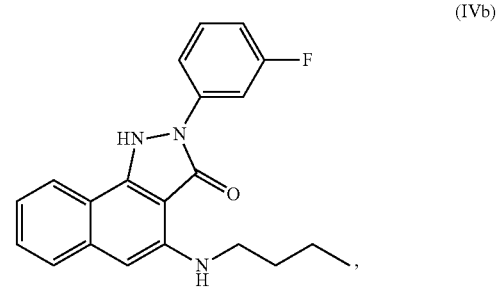

(IIIh)

wherein R* is independently at each occurrence hydrogen or a straight chained, branched, or cyclic $C_1$-$C_{20}$ hydrocarbon radical, which is saturated, partially saturated, or aromatic, each of which is optionally substituted with 1-6 heteroatoms selected from nitrogen, oxygen, sulfur, phosphorus, and halogen;

and pharmaceutically acceptable salts thereof.

21. The method of claim 1, wherein the inhibitor is a compound having a structure according to Formula IVb:

(IVb)

and pharmaceutically acceptable salts thereof.

22. The method of claim 1, wherein the inhibitor is a compound selected from Azelastine, Tetrahydrobiopterin, Silodosin, Pefloxacin, Folic acid, Pomalidomide, Mefloquine, Letrozole, Pemetrexed, Droperidol, and Ticagrelor, and pharmaceutically acceptable derivatives and salts thereof.

23. The method of claim 1, wherein the method further comprises assessing auditory, visual, or somatosensory learning and/or memory after the inhibitor administration.

24. The method of claim 7, wherein the method further comprises assessing auditory, visual, or somatosensory learning and/or memory after the inhibitor administration.

\* \* \* \* \*

SEQUENCE LISTING

<160> NUMBER OF SEQ ID NOS: 13

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gtcggtgtga acggatttg                                              19

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
tagactccac gacatactca gca                                         23

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 3 aaccccttc ctctcaaatc ca                                           22

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
cagggcgatg atcttattca cat                                                 23

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aaggagttga agtttgtgac at                                                  22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgagttggcc aaatccttgt                                                     20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acctgcctta ccaactctt                                                      19

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
attcttggct acattggtgt t                                                   21

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tacgtccaag gtcgggcagg aaga                                                24

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

```
cgatgctacc ttctgcttca tcgtatccc                                        29

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ccagaaaccc agcatcctca tctacattg                                        29

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
acatttgacc tcgtccaatt aaaagggtc                                        29

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ggaatccatg tggtgtacga tattaaccg                                        29
```